United States Patent
Cals et al.

(10) Patent No.: US 10,259,782 B2
(45) Date of Patent: Apr. 16, 2019

(54) ROR GAMMA (RORγ) MODULATORS

(71) Applicants: LEAD PHARMA HOLDING B.V., Nijmegen (NL); SANOFI, Paris (FR)

(72) Inventors: Joseph Maria Gerardus Barbara Cals, Oss (NL); Vera De Kimpe, Oss (NL); Sander Bernardus Nabuurs, Oss (NL); Cosimo Damiano Cadicamo, Oss (NL); Jaap Gerardus Henricus Lemmers, Oss (NL)

(73) Assignees: LEAD PHARMA HOLDING B.V., Nijmegen (NL); SANOFI, Paris (FR)

( * ) Notice: Subject to any disclaimer, the term of this patent is extended or adjusted under 35 U.S.C. 154(b) by 0 days.

(21) Appl. No.: 15/579,143

(22) PCT Filed: Jun. 3, 2016

(86) PCT No.: PCT/EP2016/062712
§ 371 (c)(1),
(2) Date: Dec. 1, 2017

(87) PCT Pub. No.: WO2016/193470
PCT Pub. Date: Dec. 8, 2016

(65) Prior Publication Data
US 2018/0170863 A1    Jun. 21, 2018

(30) Foreign Application Priority Data

Jun. 5, 2015    (EP) .................................. 15170764

(51) Int. Cl.
*A61K 31/167*    (2006.01)
*A61K 31/4164*    (2006.01)
(Continued)

(52) U.S. Cl.
CPC .......... *C07C 317/32* (2013.01); *A61K 31/167* (2013.01); *A61K 31/381* (2013.01);
(Continued)

(58) Field of Classification Search
CPC .............. A61K 31/167; A61K 31/4164; A61K 31/415; A61K 31/426; A61K 31/4439;
(Continued)

(56) References Cited

FOREIGN PATENT DOCUMENTS

WO    2012/100734 A1    8/2012
WO    2013/029338 A1    3/2013
(Continued)

OTHER PUBLICATIONS

Aug. 23, 2016 International Search Report issued in International Patent Application No. PCT/EP2016/062712.
(Continued)

*Primary Examiner* — Brenda L Coleman
(74) *Attorney, Agent, or Firm* — Oliff PLC

(57) ABSTRACT

Compounds according to Formula I:

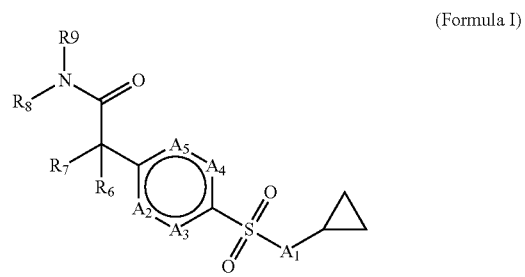

(Formula I)

or a pharmaceutically acceptable salt thereof wherein: $A_1$ is $NR_1$ or $CR_1$, with $R_1$ being H or methyl, with methyl, if present, optionally being substituted with one or more F; the cyclopropyl moiety can be optionally substituted with one or more methyl and one or more F; $A_2$-$A_5$ are N or $CR_2$-$CR_5$, respectively, with the proviso that no more than two of the four positions A in $A_2$-$A_5$ can be simultaneously N; $R_2$-$R_5$ are independently H, halogen, amino, C(1-3)alkoxy, (di)C(1-3)alkylamino or C(1-6)alkyl; $R_6$ and $R_7$ are independently H, F, methyl, ethyl, hydroxyl or methoxy or $R_2$ and $R_3$ together is carbonyl, all alkyl groups, if present, optionally being substituted with one or more F; $R_8$ is H or C(1-6)alkyl; $R_9$ is selected from the group consisting of Formula II, III, IV and V

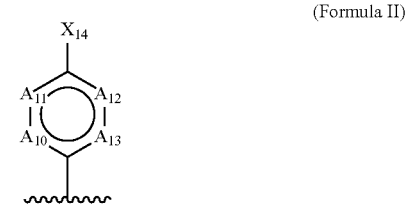

(Formula II)

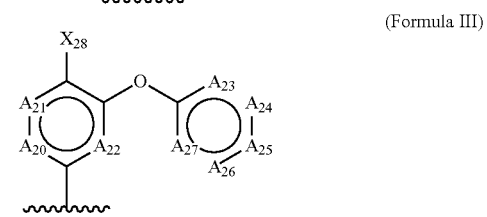

(Formula III)

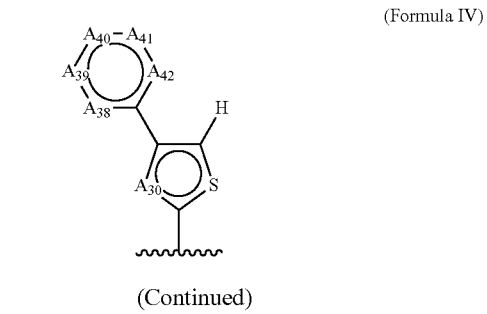

(Formula IV)

(Continued)

-continued

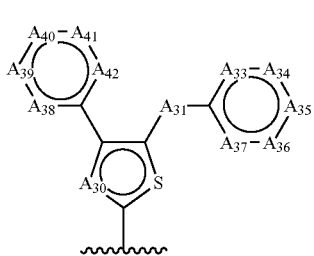

(Formula V)

The compounds can be used as inhibitors of RORγ and are useful for the treatment of RORγ mediated diseases.

16 Claims, No Drawings

(51) Int. Cl.
| | | |
|---|---|---|
| A61K 31/415 | (2006.01) | |
| A61K 31/426 | (2006.01) | |
| A61K 31/4439 | (2006.01) | |
| A61K 31/381 | (2006.01) | |
| A61K 31/4436 | (2006.01) | |
| A61K 31/4402 | (2006.01) | |
| A61K 31/4245 | (2006.01) | |
| A61K 31/421 | (2006.01) | |
| A61K 31/4196 | (2006.01) | |
| A61P 37/00 | (2006.01) | |
| A61P 29/00 | (2006.01) | |
| C07D 317/32 | (2006.01) | |
| C07D 233/61 | (2006.01) | |
| C07D 231/12 | (2006.01) | |
| C07D 277/54 | (2006.01) | |
| C07D 417/12 | (2006.01) | |
| C07D 333/36 | (2006.01) | |
| C07D 409/04 | (2006.01) | |
| C07D 213/72 | (2006.01) | |
| C07D 263/32 | (2006.01) | |
| C07D 249/08 | (2006.01) | |
| C07D 271/06 | (2006.01) | |
| C07C 317/32 | (2006.01) | |
| C07D 213/75 | (2006.01) | |
| C07C 311/20 | (2006.01) | |
| C07D 277/46 | (2006.01) | |
| C07C 317/44 | (2006.01) | |

(52) U.S. Cl.
CPC ........ *A61K 31/415* (2013.01); *A61K 31/4164* (2013.01); *A61K 31/4196* (2013.01); *A61K 31/421* (2013.01); *A61K 31/426* (2013.01); *A61K 31/4245* (2013.01); *A61K 31/4402* (2013.01); *A61K 31/4436* (2013.01); *A61K 31/4439* (2013.01); *C07C 311/20* (2013.01); *C07C 317/44* (2013.01); *C07D 213/72* (2013.01); *C07D 213/75* (2013.01); *C07D 231/12* (2013.01); *C07D 233/61* (2013.01); *C07D 249/08* (2013.01); *C07D 263/32* (2013.01); *C07D 271/06* (2013.01); *C07D 277/46* (2013.01); *C07D 277/54* (2013.01); *C07D 333/36* (2013.01); *C07D 409/04* (2013.01); *C07D 417/12* (2013.01); *C07C 2601/02* (2017.05)

(58) Field of Classification Search
CPC .............. A61K 31/381; A61K 31/4436; A61K 31/4402; A61K 31/4245; A61K 31/421; A61K 31/4196; C07D 317/32; C07D 233/61; C07D 231/12; C07D 277/54; C07D 417/12; C07D 333/36; C07D 409/04; C07D 213/72; C07D 263/32; C07D 249/08; C07D 271/06
See application file for complete search history.

(56) References Cited

FOREIGN PATENT DOCUMENTS

| | | |
|---|---|---|
| WO | 2013/171729 A2 | 11/2013 |
| WO | 2014/125426 A1 | 8/2014 |
| WO | 2014/179564 A1 | 11/2014 |
| WO | 2015/082533 A1 | 6/2015 |

OTHER PUBLICATIONS

Aug. 23, 2016 Written Opinion of the International Searching Authority issued in International Patent Application No. PCT/EP2016/062712.

ROR GAMMA (RORγ) MODULATORS

The retinoic-acid-receptor-related orphan receptor γt (RORγt) acts as a master regulator of the development of $T_H17$ cells, but also as a critical component in non-$T_H17$ IL-17 producing cells, such as for example γδ T-cells. The ROR gene family is part of the nuclear hormone receptor superfamily, and consists of three members (RORα, RORβ, and RORγ). Each gene is expressed in different isoforms, differing foremost in their N-terminal sequence. Two isoforms of RORγ have been identified: RORγ1 and RORγ2 (also known as RORγt). The term RORγ is used here to describe both RORγ1 and/or RORγ2.

The present invention relates to modulators of RORγ, to pharmaceutical compositions comprising the same and to the use of said compounds for the treatment of RORγ-mediated diseases or conditions, in particular autoimmune diseases and inflammatory diseases.

The present invention provides novel RORγ modulator compounds containing a 2-(4-cyclopropylmethanesulfonyl-phenyl)acetamide or 2-(4-cyclopropylsulfamoyl-phenyl)acetamide substructure.

The present invention relates to compounds according to Formula I

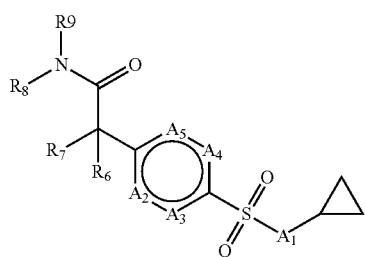

(Formula I)

or a pharmaceutically acceptable salt thereof wherein:

$A_1$ is $NR_1$ or $CR_1$, with $R_1$ being H or methyl, with methyl, if present, optionally being substituted with one or more F;

the cyclopropyl moiety can be optionally substituted with one or more methyl and one or more F;

$A_2$-$A_5$ are N or $CR_2$-$CR_5$, respectively, with the proviso that no more than two of the four positions A in $A_2$-$A_5$ can be simultaneously N;

$R_2$-$R_5$ are independently H, halogen, amino, C(1-3)alkoxy, (di)C(1-3)alkylamino or C(1-6)alkyl;

$R_6$ and $R_7$ are independently H, F, methyl, ethyl, hydroxyl or methoxy or $R_2$ and $R_3$ together is carbonyl, all alkyl groups, if present, optionally being substituted with one or more F;

$R_8$ is H or C(1-6)alkyl;

$R_9$ is selected from the group consisting of Formula II, III, IV and V

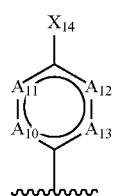

(Formula II)

wherein:

$A_{10}$-$A_{13}$ are N or $CR_{10}$-$CR_{13}$, respectively, with the proviso that no more than two of the four positions A in $A_{10}$-$A_{13}$ can be simultaneously N;

$R_{10}$-$R_{13}$ are independently H, halogen, amino, C(1-3)alkoxy, (di)C(1-3)alkylamino or C(1-6)alkyl;

$X_{14}$ is either C(6-10)aryl or C(1-9)heteroaryl, with all carbon atoms optionally substituted with halogen, amino, cyano, C(1-3)alkoxy, (di)C(1-3)alkylamino or C(1-3)alkyl;

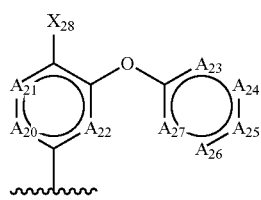

(Formula III)

wherein:

$A_{20}$-$A_{27}$ are N or $CR_{20}$-$CR_{27}$ respectively, with the proviso that no more than two of the three positions A in $A_{20}$-$A_{22}$ can be simultaneously N and that no more than three of the five positions A in $A_{23}$-$A_{27}$ can be simultaneously N;

$R_{20}$-$R_{22}$ are independently H, halogen, amino, C(1-3)alkoxy, (di)C(1-3)alkylamino or C(1-6)alkyl;

$R_{23}$-$R_{27}$ are independently H, halogen, amino, cyano, C(1-3)alkoxy, (di)C(1-3)alkylamino or C(1-3)alkyl;

$X_{28}$ is either C(6-10)aryl or C(1-9)heteroaryl, with all carbon atoms optionally substituted with halogen, amino, cyano, C(1-3)alkoxy, (di)C(1-3)alkylamino or C(1-3)alkyl;

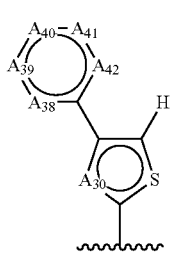

(Formula IV)

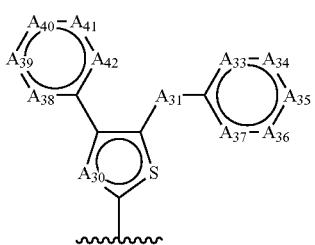

(Formula V)

wherein:

$A_{30}$ is N or C;

$A_{31}$ is O, carbonyl, $NR_{31}$ or $CR_{32}$;

$R_{31}$ is H or C(1-6)alkyl;

$R_{32}$ is either H, OH, or C(1-3)alkyl, with all alkyl groups optionally substituted with one or more F or OH;

$A_{33}$-$A_{42}$ are N or $CR_{33}$-$CR_{42}$ respectively, with the proviso that no more than three of the five positions A in $A_{33}$-$A_{37}$ can be simultaneously N and that no more than three of the five positions A in $A_{38}$-$A_{42}$ can be simultaneously N;

$R_{33}$-$R_{42}$ are independently H, halogen, amino, cyano, C(1-3)alkoxy, (di)C(1-3)alkylamino or C(1-3)alkyl.

The term C(1-6)alkyl as used herein means a branched or unbranched alkyl group having 1-6 carbon atoms, for example methyl, ethyl, propyl, isopropyl, butyl, tert-butyl, n-pentyl and n-hexyl. All carbon atoms may optionally be substituted with one or more halogen.

The term C(1-3)alkyl as used herein means an alkyl group having 1-3 carbon atoms, i.e. methyl, ethyl, propyl or isopropyl. All carbon atoms may optionally be substituted with one or more halogen.

The term C(1-2)alkyl as used herein means an alkyl group having 1-2 carbon atoms i.e. methyl or ethyl. All carbon atoms may optionally be substituted with one or more halogen.

The term C(6-10)aryl as used herein means an aromatic hydrocarbon group having 6-10 carbon atoms, for example phenyl or naphthyl. The preferred aromatic hydrocarbon group is phenyl. All carbon atoms may optionally be substituted with one or more halogen.

The term C(6)aryl as used herein means an aromatic hydrocarbon group having 6 carbon atoms, i.e. phenyl. All carbon atoms may optionally be substituted with one or more halogen.

The term heteroatom as used herein refers to a nitrogen, sulfur or oxygen atom.

The term amino as used herein refers to an $NH_2$ group.

The term C(1-9)heteroaryl as used herein means an aromatic group having 1-9 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, isoxazolyl, tetrazolyl and quinolyl. All carbon atoms may optionally be substituted with one or more halogen or methyl.

The term C(1-5)heteroaryl as used herein means an aromatic group having 1-5 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, isoxazolyl, and tetrazolyl. All carbon atoms may optionally be substituted with one or more halogen or methyl.

The term cyclopropylmethyl as used herein means a methyl group substituted with cyclopropyl. All carbon atoms are optionally substituted with one or more halogen or methyl.

The term (di)C(1-3)alkylamino as used herein means an amino group, which is monosubstituted or disubstituted with a C(1-3)alkyl group, the latter having the same meaning as previously defined.

The term C(1-3)alkoxy means an alkoxy group having 1-3 carbon atoms, the alkyl moiety being branched or unbranched. All carbon atoms are optionally substituted with one or more F.

The term halogen as used herein means Cl or F.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt represents those salts which are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one embodiment the invention relates to a compound according to Formula I wherein $A_1$ is $CR_1$.

In another embodiment the invention relates to a compound according to Formula I wherein $A_1$ is $NR_1$.

In another embodiment the invention relates to a compound according to Formula I wherein $R_1$ is hydrogen.

In another embodiment the invention relates to a compound according to Formula I wherein $R_6$ and $R_7$ are independently H, methyl or hydroxyl.

In yet another embodiment the invention relates to a compound according to Formula I wherein $R_6$ and $R_7$ are both H.

The invention also relates to a compound according to Formula I wherein $R_8$ is H or C(1-2)alkyl, H being the most preferred.

The invention also relates to a compound according to Formula I wherein $R_8$ is H.

In yet another embodiment the invention relates to a compound according to Formula I wherein $R_2$ is methyl and $R_3$-$R_5$ are H.

In another embodiment the invention relates to a compound according to Formula I wherein $R_2$-$R_5$ are H.

In another embodiment the invention relates to a compound according to Formula I wherein all positions A in $A_2$-$A_5$ are $CR_2$-$R_5$.

In yet another embodiment the invention relates to a compound according to Formula I wherein all positions A in $A_2$-$A_5$ are $CR_2$-$R_5$, and all positions R in $R_2$-$R_5$ are H.

In again another embodiment the invention relates to a compound according to Formula I where $R_9$ is according to Formula II wherein: $A_{10}$-$A_{13}$ are N or $CR_{10}$-$CR_{13}$, respectively, with the proviso that no more than two of the four positions A in $A_{10}$-$A_{13}$ can be simultaneously N; $R_{10}$-$R_{13}$ are independently H, amino, halogen, C(1-3)alkoxy, (di)C(1-3)alkylamino or C(1-6)alkyl; $X_{14}$ is either C(6)aryl or C(1-5)heteroaryl, with all carbon atoms optionally substituted with halogen, cyano, C(1-3)alkoxy, (di)C(1-3)alkylamino or C(1-3)alkyl, of which optional substituent C(1-3)alkoxy is preferred.

In again another embodiment the invention relates to a compound according to Formula I wherein $R_9$ is according to Formula II and all positions A in $A_{10}$-$A_{13}$ are carbon.

In another embodiment the invention relates to a compound according to Formula I wherein $R_9$ is according to Formula II and $A_{10}$ is nitrogen.

In another embodiment the invention relates to a compound according to Formula I wherein $R_9$ is according to Formula II and $A_{11}$ is nitrogen.

The invention also relates to a compound according to Formula I wherein $R_9$ is according to Formula II and $R_{10}$-$R_{13}$ are independently H, halogen, methyl or methoxy.

In another embodiment the invention relates to a compound according to Formula I wherein $R_9$ is according to Formula II and $R_{10}$-$R_{13}$ are H.

In yet another embodiment the invention relates to a compound according to Formula I wherein $R_9$ is according to Formula II and $X_{14}$ is C(6)aryl, with all carbon atoms optionally substituted with halogen, cyano, C(1-3)alkoxy, (di)C(1-3)alkylamino or C(1-3)alkyl.

In yet another embodiment the invention relates to a compound according to Formula I wherein $R_9$ is according to Formula II and $X_{14}$ is C(1-5)heteroaryl, with all carbon atoms optionally substituted with halogen, cyano, C(1-3)alkoxy, (di)C(1-3)alkylamino or C(1-3)alkyl.

In again another embodiment the invention relates to a compound according to Formula I wherein $R_9$ is according to Formula II and $X_{14}$ is C(6)aryl or C(1-5)heteroaryl, with all carbon atoms optionally substituted with C(1-3)alkoxy.

In yet another embodiment the invention relates to a compound according to Formula I wherein $R_9$ is according to Formula II and $X_{14}$ is 2-(trifluoromethoxy)phenyl.

In again another embodiment the invention relates to a compound according to Formula I where $R_9$ is according to Formula III wherein: $A_{20}$-$A_{27}$ are N or $CR_{20}$-$CR_{27}$ respectively, with the proviso that no more than two of the three positions A in $A_{20}$-$A_{22}$ can be simultaneously N and that no more than three of the five positions A in $A_{23}$-$A_{27}$ can be simultaneously N; $R_{20}$-$R_{22}$ are independently H, halogen, amino, C(1-3)alkoxy, (di)C(1-3)alkylamino or C(1-6)alkyl; $R_{23}$-$R_{27}$ are independently H, halogen, cyano, amino, C(1-3)alkoxy, (di)C(1-3)alkylamino or C(1-3)alkyl; $X_{28}$ is either C(6)aryl or C(1-5)heteroaryl, with all carbon atoms optionally substituted with halogen, cyano, C(1-3)alkoxy, (di)C(1-3)alkylamino or C(1-3)alkyl.

In again another embodiment the invention relates to a compound according to Formula I wherein $R_9$ is according to Formula III and all positions A of $A_{20}$-$A_{22}$ are carbon.

In again another embodiment the invention relates to a compound according to Formula I wherein $R_9$ is according to Formula III and $A_{20}$ is nitrogen.

In yet another embodiment the invention relates to a compound according to Formula I wherein $R_9$ is according to Formula III and $A_{22}$ is nitrogen.

In again another embodiment the invention relates to a compound according to Formula I wherein $R_9$ is according to Formula III and $R_{20}$-$R_{22}$ are independently H, halogen, methyl or methoxy.

In again another embodiment the invention relates to a compound according to Formula I wherein $R_9$ is according to Formula III and $R_{20}$-$R_{22}$ are H.

In another embodiment the invention relates to a compound according to Formula I wherein $R_9$ is according to Formula III and all positions A of $A_{23}$-$A_{27}$ are carbon.

In another embodiment the invention relates to a compound according to Formula I wherein $R_9$ is according to Formula III and $R_{23}$, $R_{25}$ and $R_{27}$ are H.

The invention also relates to a compound according to Formula I wherein $R_9$ is according to Formula III and $R_{24}$ and $R_{26}$ are independently H, halogen, cyano, methoxy or methyl.

In another embodiment the invention relates to a compound according to Formula I wherein $R_9$ is according to Formula III and $X_{28}$ is C(6)aryl, with all carbon atoms optionally substituted with halogen, cyano, C(1-3)alkoxy, (di)C(1-3)alkylamino or C(1-3)alkyl.

In again another embodiment the invention relates to a compound according to Formula I wherein $R_9$ is according to Formula III and $X_{28}$ is C(1-5)heteroaryl, with all carbon atoms optionally substituted with halogen, cyano, C(1-3)alkoxy, (di)C(1-3)alkylamino or C(1-3)alkyl.

In yet another embodiment the invention relates to a compound according to Formula I wherein $R_9$ is according to Formula III and $X_{28}$ is phenyl.

In again another embodiment the invention relates to a compound according to Formula I wherein $R_9$ is according to Formula III and $X_{28}$ is a 1H-imidazol-1-yl group.

In another embodiment the invention relates to a compound according to Formula I wherein $R_9$ is according to Formula III and $X_{28}$ is a 1H-pyrazol-1-yl group.

In again another embodiment the invention relates to a compound according to Formula I wherein $R_9$ is according to Formula IV or V wherein: $A_{30}$ is N or C; $A_{31}$ is O, carbonyl, $NR_{31}$ or $CR_{32}$; $R_{31}$ is H or C(1-6)alkyl; $R_{32}$ is H, OH or C(1-6)alkyl, with all alkyl groups optionally substituted with one or more F or OH; $A_{33}$-$A_{42}$ are N or $CR_{33}$-$CR_{42}$ respectively, with the proviso that no more than three of the five positions $A_{33}$-$A_{37}$ can be simultaneously N and that no more than three of the five positions $A_{38}$-$A_{42}$ can be simultaneously N; $R_{33}$-$R_{42}$ are independently H, halogen, cyano, C(1-3)alkoxy, (di)C(1-3)alkylamino or C(1-3)alkyl.

The invention also relates to a compound according to Formula I wherein $R_9$ is according to Formula IV or V and $A_{30}$ is N.

The invention also relates to a compound according to Formula I wherein $R_9$ is according to Formula IV or V and $A_{30}$ is C.

In another embodiment the invention relates to a compound according to Formula I wherein $R_9$ is according to Formula V and $A_{31}$ is carbonyl.

In another embodiment the invention relates to a compound according to Formula I wherein $R_9$ is according to Formula V and $A_{31}$ is oxygen.

In yet another embodiment the invention relates to a compound according to Formula I wherein $R_9$ is according to Formula V and all positions A of $A_{33}$-$A_{42}$ are carbon.

The invention also relates to those compounds wherein all specific definitions for $A_1$ through $A_{42}$, $R_1$ through $R_{42}$, and all substituent groups in the various aspects of the inventions defined here above occur in any combination within the definition of the compound of Formula I.

In another aspect the invention relates to compounds of Formula I, which have a pIC50 of 5 or higher. In yet another aspect the invention relates to compounds according to Formula I with a pIC50 of more than 6. In yet another aspect the invention relates to compounds according to Formula I with a pIC50 of more than 7. In yet another aspect the invention relates to compounds according to Formula I with a pIC50 of more than 8.

In yet another aspect the invention resides in the compounds according to Formula I selected as described in examples 1-47.

The compounds of Formula I may form salts, which are also within the scope of this invention. Reference to a compound of Formula I herein is understood to include reference to salts thereof, unless otherwise indicated.

The compounds of Formula I may contain asymmetric or chiral centers and, therefore, exist in different stereoisomeric forms. It is intended that all stereoisomeric forms of the compounds of Formula I as well as mixtures thereof, including racemic mixtures, form part of the present invention.

Diastereomeric mixtures can be separated into their individual diastereomers on the basis of their physical chemical differences by methods well known to those skilled in the art, such as, for example, chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Enantiomers can also be separated by use of chiral HPLC column.

The skilled artisan will recognize that desirable IC50 values are dependent on the compound tested. For example, a compound with an IC50 value less than $10^{-5}$ M is generally considered a candidate for drug selection. Preferably, this value is lower than $10^{-6}$ M. However, a compound which has a higher IC50 value, but is selective for the particular receptor, may be even a better candidate.

The compounds of the invention inhibit RORγ activity. Modulation of RORγ activity can be measured using for example biophysical (natural) ligand displacement studies, biochemical AlphaScreen or FRET assays, cellular GAL4 reporter gene assays, cellular IL-17 promotor reporter assay or functional IL-17 ELISA assays using for example mouse splenocytes or human peripheral blood mononuclear cells (PBMCs) cultured under $T_H17$ polarizing conditions.

In such assays, the interaction of a ligand with RORγ can be determined by measuring, for example, the ligand modulated interaction of cofactor-derived peptides with the RORγ ligand binding domain, or measuring the gene products of ligand modulated RORγ mediated transcription using, for example, luciferase reporter assays or IL-17 ELISA assays.

The present invention also relates to a pharmaceutical composition comprising compounds or pharmaceutically acceptable salts thereof having the general Formula I in admixture with pharmaceutically acceptable excipients and optionally other therapeutically active agents. The excipients must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable excipients, the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple sub-doses administered at appropriate intervals throughout the day.

The compounds according to the invention can be used in therapy.

A further aspect of the invention resides in the use of compounds according to the invention or a pharmaceutically acceptable salt thereof for the treatment of RORγ-mediated diseases or RORγ mediated conditions.

Another aspect of the invention resides in the use of compounds having the general Formula I or a pharmaceutically acceptable salt thereof for the treatment of autoimmune diseases, in particular those diseases in which $T_H17$ cells and non-$T_H17$ cells, which express $T_H17$ hallmark cytokines play a prominent role. These include, but are not limited to, the treatment of rheumatoid arthritis, psoriasis, inflammatory bowel disease, Crohn's disease and multiple sclerosis.

In another aspect, compounds having the general Formula I or a pharmaceutically acceptable salt thereof can be used for treatment of inflammatory diseases in which $T_H17$ cells and/or non-$T_H17$ cells, which express $T_H17$ hallmark cytokines play a prominent role such as, but not limited to respiratory diseases, osteoarthritis and asthma. Also, compounds or a pharmaceutically acceptable salt thereof having the general Formula I can be used for treatment of infectious diseases in which $T_H17$ cells and/or non-$T_H17$ cells, which express $T_H17$ hallmark cytokines play a prominent role such as, but not limited to mucosal leishmaniasis.

Compounds having the general Formula I or a pharmaceutically acceptable salt thereof can also be used for treatment of other diseases in which $T_H17$ cells and/or non-$T_H17$ cells, which express $T_H17$ hallmark cytokines play a prominent role such as, but not limited to Kawaski disease and Hashimoto's thyroiditis.

In yet another aspect the invention resides in the use of compounds having the general Formula I for the treatment of multiple sclerosis, inflammatory bowel disease, Crohn's disease, psoriasis, rheumatoid arthritis, asthma, osteoarthritis, Kawaski disease, Hashimoto's thyroiditis, cancer and mucosal leishmaniasis.

In another aspect, the compounds according to the invention can be used in therapies to treat or prevent multiple sclerosis, inflammatory bowel disease, Crohn's disease, psoriasis and rheumatoid arthritis, asthma, osteoarthritis, Kawaski disease, Hashimoto's thyroiditis, cancer and mucosal leishmaniasis.

In another aspect the compounds according to the invention can be used to treat or prevent psoriasis.

In yet another aspect the compounds according to the invention can be used to treat inflammatory bowel disease.

The invention is illustrated by the following examples.

EXEMPLIFICATION

As depicted in the Examples below, in certain exemplary embodiments, compounds are prepared according to the following general procedures. It will be appreciated that, although the general methods depict the synthesis of certain compounds of the invention, the following general methods, and other methods known to one skilled in the art, can be applied to all compounds and subclasses and species of each of these compounds, as described herein.

General Methods of Preparation

The compounds described herein, including compounds of general Formula A, B and I can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those skilled in the art, but are not mentioned in greater detail. For example, where specific acids, bases, reagents, coupling agents, solvents, etc. are mentioned, it is understood that other suitable acids, bases, reagents, coupling agents, solvents etc. may be used and are included within the scope of the present invention. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxyl, thiol and carboxylic acid groups that may interfere with the desired reaction, it may be advantageous to employ protected forms of the intermediate. Methods for the selection, introduction and subsequent removal of protecting groups are well known to those skilled in the art. The compounds obtained by using the general reaction sequences may be of insufficient purity. The compounds can be purified by using any of the methods for purification of organic compounds, for example, crystallization or silica gel or alumina column chromatography, using different solvents in suitable ratios. All possible stereoisomers are envisioned within the scope of the invention. In the discussion below variables have the meaning indicated above unless otherwise indicated.

The abbreviations used in these experimental details are listed below and additional ones should be considered known to a person skilled in the art of synthetic chemistry.

Abbreviations used herein are as follow: r.t.: room temperature; HATU: 2-(7-Aza-1H-benzotriazole-1-yl)-1,1,3,3-tetramethyluronium hexafluorophosphate; DMF: Dimethyl formamide; DiPEA: Diisopropylethylamine; DMAP: 4-(dimethylamino)pyridine; DCC: N,N'-Dicyclohexylcarbodiimide; mCPBA: 3-chloroperoxybenzoic acid; TFA: Trifluoroacetic acid; TFAA: Trifluoroacetic anhydride; THF: Tetrahydrofuran; DMSO: Dimethylsulfoxide; PTSA: p-Toluenesulfonic acid; PyBOP: (Benzotriazol-1-yloxy)tripyrrolidinophosphonium hexafluorophosphate; EtOH: Ethanol; TLC: Thin Layer Chromatography; Ph3P: Triphenyl phosphine; EDCI: 1-Ethyl-3-(3-dimethylaminopropyl)carbodiimide; BuLi: n-Butyl lithium; $PdCl_2(dppf)$: [1,1'-Bis(diphenylphosphino)ferrocene]palladium(II) dichloride.

Chemical names are preferred IUPAC names, generated using MarvinSketch version 6.3.0.

If a chemical compound is referred to using both a chemical structure and a chemical name, and an ambiguity exists between the structure and the name, the structure predominates.

General Procedures

Scheme 1:

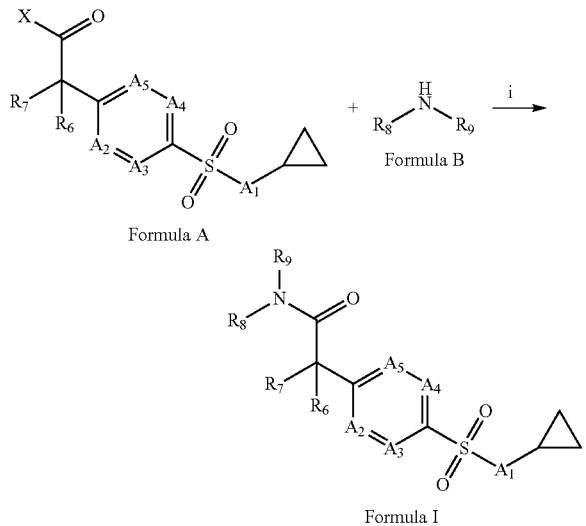

Conditions: i) EDCl, DMAP, $CH_2Cl_2$.

As depicted in scheme 1, the derivatives of the invention having Formula I can be prepared by methods known in the art of organic chemistry. Compounds of the invention can for example be obtained by an amide coupling reaction between a Formula A phenylacetic acid derivative (X is OH), wherein $R_2$, $R_3$, $R_5$, $R_6$, $R_7$, $R_8$, and $A_1$ have the meaning as previously described, and a Formula B amine derivative, wherein $R_8$, and $R_9$ have the meaning as previously described, using a coupling reagent such as EDCI, HATU, DCC, or PyBOP or the like, in the presence of a suitable base such as DiPEA or catalyst such as DMAP.

Alternatively, a Formula A phenylacetic acid derivative (X=OH) can be converted into a Formula A acid chloride derivative (X=Cl), using for example $SOCl_2$ or oxalyl chloride. The obtained Formula A acid chloride derivative ($X_1$=Cl), wherein $R_2$, $R_3$, $R_5$, $R_8$, $R_7$, $R_8$, and $A_1$, have the meaning as previously described, can be coupled, in the presence of a suitable base such as $Et_3N$ or the like, with a Formula B amine derivative, wherein $R_8$ and $R_9$ have the meaning as previously described.

Scheme 2:

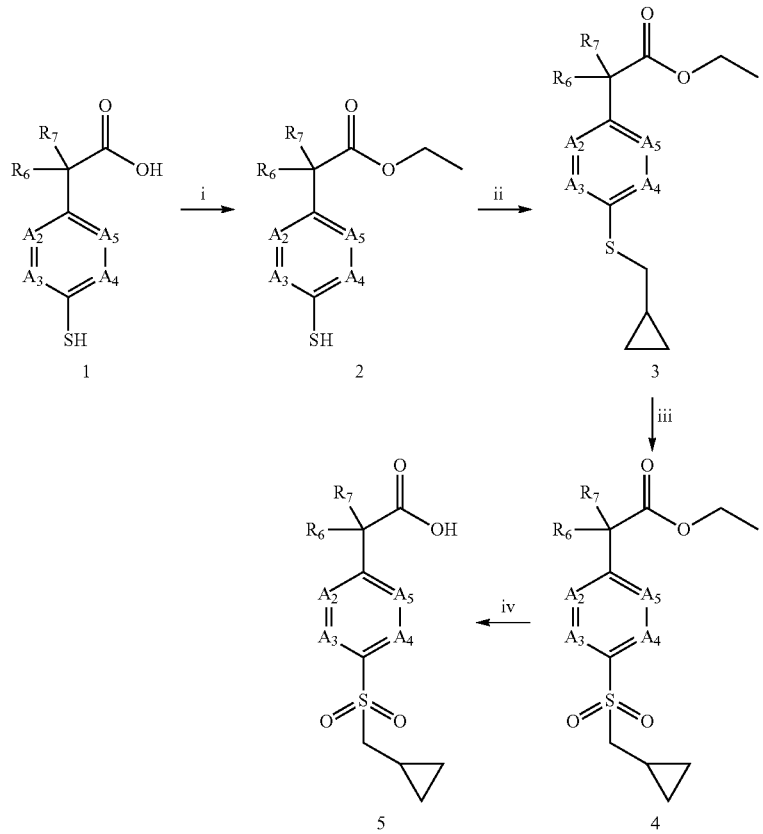

Conditions: i) $H_2SO_4$, EtOH, 60° C.; ii) (bromomethyl)cyclopropane, $K_2CO_3$, $CH_3CN$, r.t.; iii) mCPBA, $CH_2Cl_2$, r.t.; iv) 2N NaOH, EtOH, r.t.

Scheme 2 illustrates a general method for preparing Formula A 2-(4-cyclopropylmethanesulfonylphenyl)acetic acid derivatives 5 wherein $A_1$ is $CH_2$ and $A_2$, $A_3$, $A_4$, $A_5$, $R_6$, and $R_7$ have the meaning as previously described.

Esterification of 4-mercaptophenylacetic acid derivatives 1 under acidic conditions, using for example $H_2SO_4$ in ethanol, provides ethyl 4-mercaptophenylacetate derivatives 2. Alkylation of the sulfur group using (bromomethyl) cyclopropane in the presence of a base, such as $K_2CO_3$, gives the corresponding ethyl 2-(4-cyclopropylmethanesulfanylphenyl)acetate derivatives 3. Oxidation, using e.g. mCPBA, gives ethyl 2-(4-cyclopropylmethanesulfonylphenyl)acetate derivatives 4 which after saponification of the ester moiety under basic conditions, e.g. NaOH in ethanol, gives the corresponding Formula A derivatives 5.

Scheme 3:

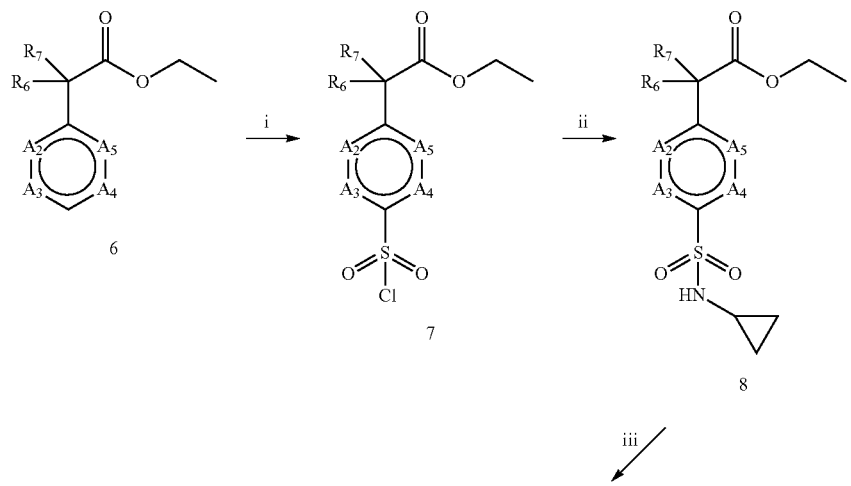

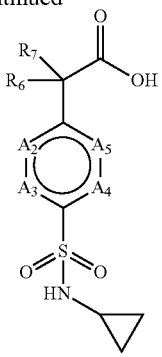

8

Conditions: i) Chlorosulfonic acid, CH$_2$Cl$_2$, 0° C. to r.t.; ii) Cyclopropylamine, Et$_3$N, CH$_2$Cl$_2$, r.t.; iii) 2N NaOH, EtOH, r.t.

Scheme 3 illustrates a general method for preparing Formula A 2-[4-(cyclopropylsulfamoyl)phenyl]acetic acid derivatives 9 wherein A$_1$ is NH and A$_2$, A$_3$, A$_4$, A$_5$, R$_6$, and R$_7$ have the meaning as previously described.

Reaction of ethyl 2-phenylacetate derivatives 6 with chlorosulfonic acid provides ethyl 2-[4-(chlorosulfonyl)phenyl]acetate derivatives 7 which after nucleofilic substitution with cyclopropyl amine gives ethyl 2-[4-(cyclopropylsulfamoyl)phenyl]acetate derivatives 8. Saponification of the ester moiety under basic conditions, e.g. NaOH in ethanol, gives the corresponding Formula A derivatives 9.

Most of the Compounds of Formula B are Commercially Available, Known or Prepared According to Methods Known to those Skilled in the Art.

Scheme 4:

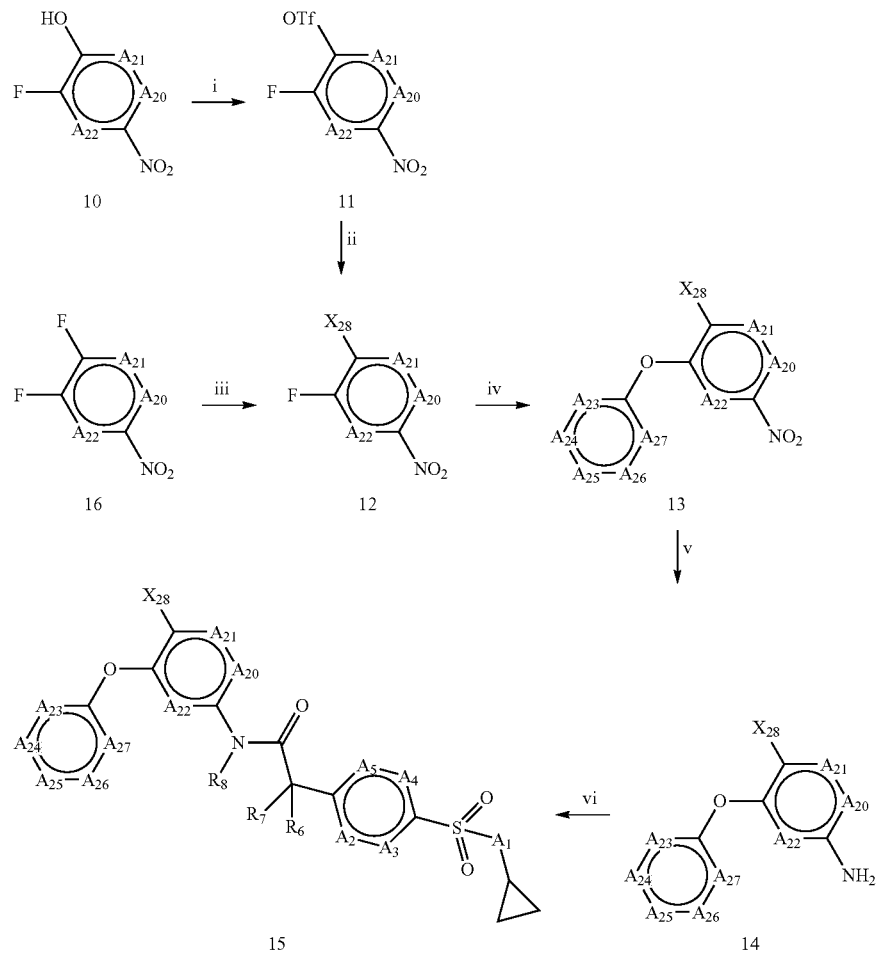

Conditions: i) Trifluoromethanesulfonic anhydride, CH$_2$Cl$_2$, pyridine, DMAP. r.t.; ii) A suitable boronic acid, Pd(Ph$_3$)$_4$, K$_2$CO$_3$, EtOH, water, reflux; iii) A suitable heteroaryl, K$_2$CO$_3$, DMF, 150° C.; iv) Cs$_2$CO$_3$, A suitable phenol, DMF, 110° C.; v) Zinc powder, NH$_4$Cl, THF, water 75° C.; vi) 5 or 9, EDCl, DMAP, CH$_2$Cl$_2$, 60° C.

Scheme 4 demonstrates general methods for the preparation of Formula I derivatives 15 wherein $R_6$, $R_7$, $R_8$, $A_1$, $A_2$, $A_3$, $A_4$, $A_5$, $A_{20}$, $A_{21}$, $A_{22}$, $A_{23}$, $A_{24}$, $A_{25}$, $A_{26}$, $A_{27}$, and $X_{28}$ have the meaning as previously described.

2-fluoro-4-nitrophenol derivatives 10 on reaction with trifluoromethanesulfonic anhydride in the presence of a suitable base such as pyridine gives the corresponding triflate derivatives 11 which under Suzuki-coupling reaction conditions with an appropriate aryl boronic acid or heteroaryl boronic acid, in the presence of a catalyst such as Pd(Ph$_3$P)$_4$ and a base such as K$_2$CO$_3$, affords the corresponding biaryl derivatives 12. To obtain nitrogen-coupled heteroaromatic derivatives of Formula I, 1,2-difluoro-4-nitrobenzene derivatives 16 can react with a suitable heteroaryl compound, in the presence of a base e.g. K$_2$CO$_3$, to afford the corresponding biaryl derivatives 12. On reaction with an appropriate phenol, using a base such as Cs$_2$CO$_3$, derivatives 12 afford the corresponding aryl ether derivatives 13. The nitro group of derivatives 13 can be reduced, by using for example NH$_4$Cl in the presence of zinc or iron, to afford the Formula B amine derivatives 14, wherein $R_4$ is hydrogen, which can be condensed with Formula A derivatives 5 or 9, in the presence of for example EDCI and DMAP, giving Formula I derivatives 15.

Scheme 5:

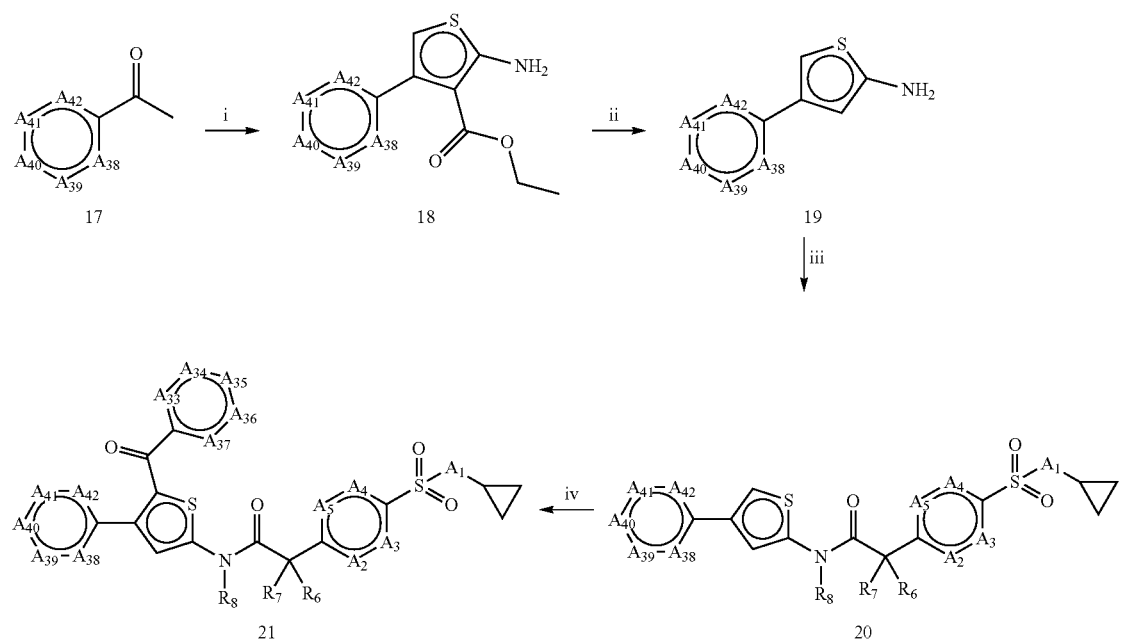

Conditions: i) Ethyl 2-cyanoacetate, sulfur, morpholine, EtOH, reflux; ii) NaOH, EtOH, reflux; iii) 5 or 9, EDCI, DMAP, CH$_2$Cl$_2$, 60° C.; iv) Suitable benzoyl chloride, SnCl$_4$, CH$_2$Cl$_2$, reflux.

Scheme 5 represents a general method for the preparation of Formula I derivatives 21 wherein $A_{30}$ is C, $A_{31}$ is carbonyl and $R_6$, $R_7$, $R_8$, $A_1$, $A_2$, $A_3$, $A_4$, $A_5$, $A_{33}$, $A_{34}$, $A_{35}$, $A_{36}$, $A_{37}$, $A_{38}$, $A_{39}$, $A_{40}$, $A_{41}$, and $A_{42}$ have the meaning as previously described.

Substituted phenyl methyl ketones 17 can be reacted with ethyl 2-cyanoacetate and sulfur in the presence of morpholine to form the corresponding thiophene esters 18. De-esterification of compound 18 provides thiophene amino Formula B derivatives 19, which can be condensed with a phenylacetic acid derivative of Formula A, in the presence of for example EDCI and DMAP, to afford the corresponding Formula I thiophene amide derivatives 20. Acylation of the thiophene ring catalyzed by SnCl$_4$ or AlCl$_3$, gives Formula I derivatives 21.

Scheme 6:

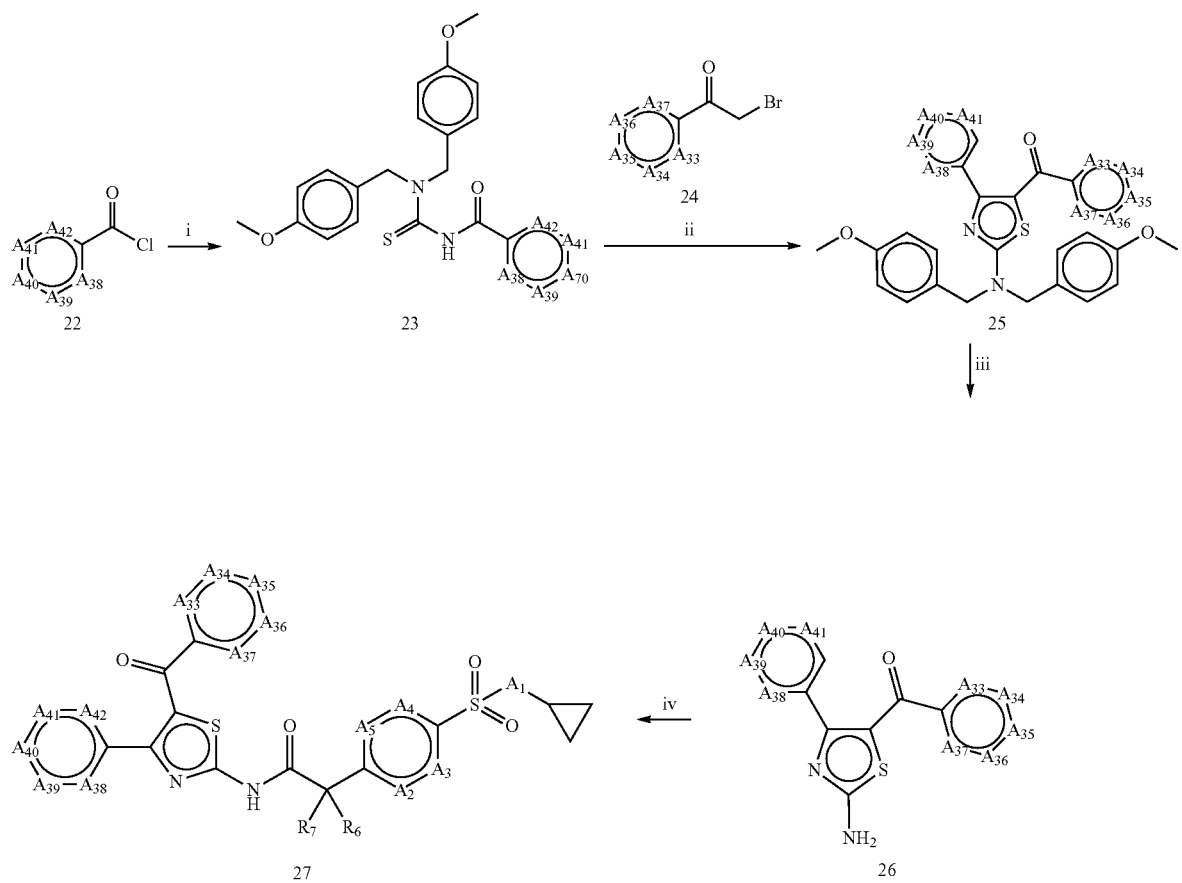

Conditions: i) bis[(4-methoxyphenyl)methyl]amine, NH₄SCN, acetone, 0° C.; ii) DMF, 85° C.; iii) TFA, 80° C.; iv) 5 or 9, EDCl, DMAP, CH₂Cl₂, 60° C.

Scheme 6 depicts a general reaction scheme for the preparation of Formula I derivatives 27 wherein $A_{30}$ is nitrogen, $A_{31}$ is carbonyl and $R_6$, $R_7$, $A_1$, $A_2$, $A_3$, $A_4$, $A_5$, $A_{33}$, $A_{34}$, $A_{35}$, $A_{36}$, $A_{37}$, $A_{38}$, $A_{39}$, $A_{40}$, $A_{41}$ and $A_{42}$ have the meaning as previously described.

The protected carbamothioyl amide derivatives 23 can be obtained by condensation of acyl chlorides 22, thiocyanate and bis[(4-methoxyphenyl)methyl]amine. Reaction between the protected carbamothioyl amide derivatives 23 and appropriate α-bromo ketones 24, which can be obtained commercially or synthesized starting from methyl ketones, by using methods known to those skilled in the art, affords the protected thiazole ketone derivatives 25. Deprotection under acidic conditions, using for example TFA, gives the Formula B 2-aminothiazole derivatives 26, which can be condensed with Formula A derivatives 5 or 9, in the presence of for example EDCI and DMAP giving Formula I derivatives 27

Scheme 7:

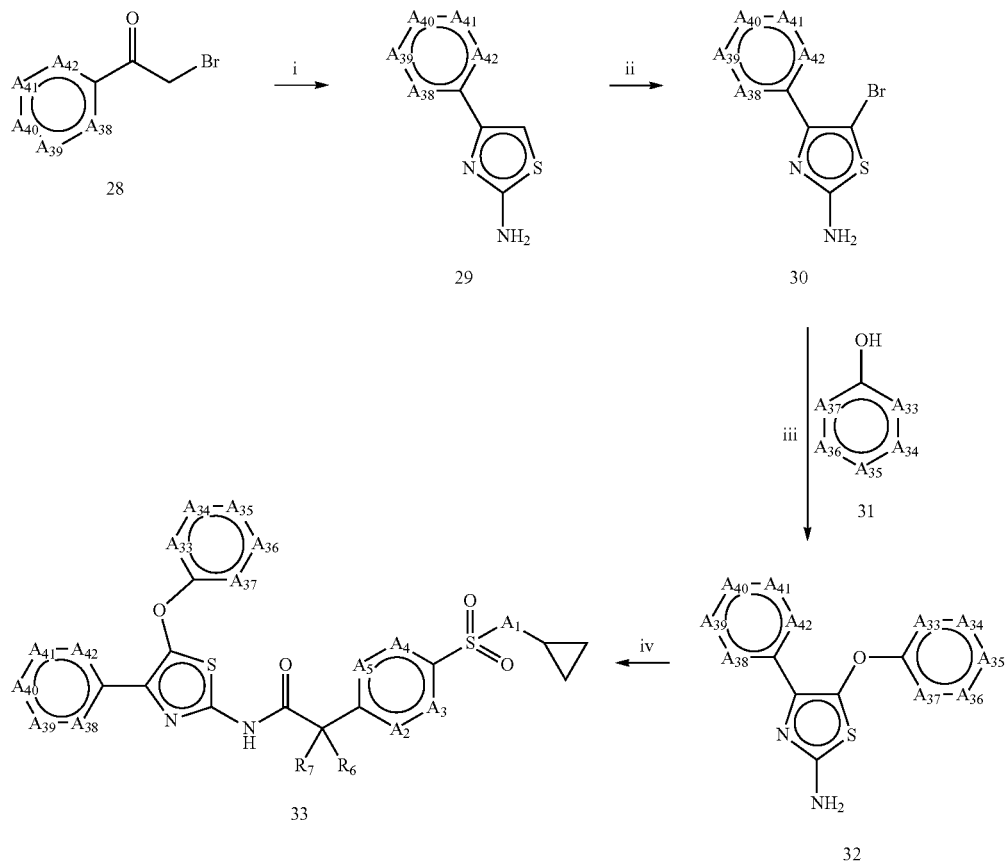

Conditions: i) Thiourea, EtOH, 80° C.; ii) CuBr$_2$, CH$_3$CN, r.t.; iii) suitable phenol, Cs$_2$CO$_3$, acetone, 55° C.; iv) 5 or 9, EDCl, DMAP, CH$_2$Cl$_2$, 60° C.

Scheme 7 depicts a general reaction scheme the preparation of Formula I derivatives 33 wherein A$_{30}$ is nitrogen, A$_{31}$ is oxygen and R$_6$, R$_7$, A$_1$, A$_2$, A$_3$, A$_4$, A$_5$, A$_{33}$, A$_{34}$, A$_{35}$, A$_{36}$, A$_{37}$, A$_{38}$, A$_{39}$, A$_{40}$, A$_{41}$ and A$_{42}$ have the meaning as previously described. On reaction with thiourea, α-bromo ketone derivatives 28 afford 1,3-thiazol-2-amine derivatives 29 which after bromination, in the presence of CuBr$_2$, give 5-bromo-1,3-thiazol-2-amine derivatives 30. Substitution of the bromine by a suitable phenol 31 affords the Formula B thiazolo derivatives 32 which can be condensed with Formula A derivatives 5 or 9, in the presence of for example EDCI and DMAP giving Formula I derivatives 33.

All building blocks used are commercially available, known or prepared according to methods known to those skilled in the art.

EXAMPLES

Examples 1-47

1: 2-(4-cyclopropylmethanesulfonylphenyl)-N-(3-phenoxy-4-phenylphenyl)acetamide

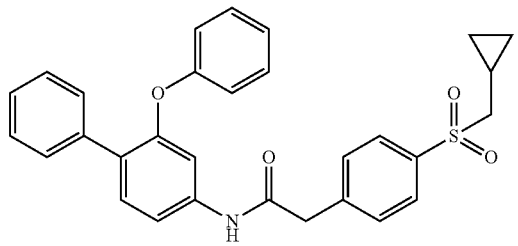 [SMILES: O=C(Cc1ccc(S(=O)(=O)CC2CC2)cc1)Nc1ccc(-c2ccccc2)c(Oc2ccccc2)c1]

i) To a solution of 2-(4-cyclopropylmethanesulfonylphenyl)acetic acid (29 mg), 3-phenoxy-4-phenylaniline (30 mg) and DMAP (3 mg) in CH$_2$Cl$_2$ (0.5 mL) was added dropwise at 0° C. a solution of EDCI (32 mg) in CH$_2$Cl$_2$. The reaction mixture was stirred at 60° C. for 1 hour in a microwave. After cooling to room temperature, the organic layer was washed with a saturated aqueous NaHCO$_3$ solution, water then brine, dried over MgSO$_4$ and concentrated under reduced pressure. The residue was purified on SiO$_2$, using 1% to 10% methanol in CH$_2$Cl$_2$ as the eluent, giving the title compound 2-(4-cyclopropylmethanesulfonylphenyl)-N-(3-phenoxy-4-phenylphenyl)acetamide (70 mg) as a white solid. MS(ES$^+$) m/z 498.2 (M+H)$^+$.

Following a procedure described for Example 1, the following compounds have been prepared.

2: 2-(4-cyclopropylmethanesulfonylphenyl)-N-[4-(3-fluorophenyl)-3-(3-methoxyphenoxy)phenyl]acetamide

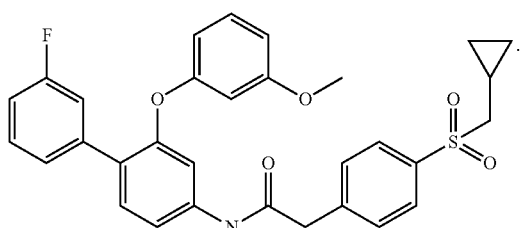

MS(ES$^+$) m/z 546.2 (M + H)$^+$

3: 2-(4-cyclopropylmethanesulfonylphenyl)-N-[3-(3-methoxyphenoxy)-4-(4-methyl-1H-imidazol-1-yl)phenyl]acetamide

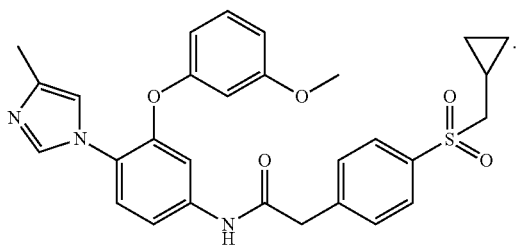

MS(ES⁺) m/z 532.2 (M + H)⁺

4: N-[3-(3-chlorophenoxy)-4-(3-fluorophenyl)phenyl]-2-(4-cyclopropylmethanesulfonylphenyl)acetamide

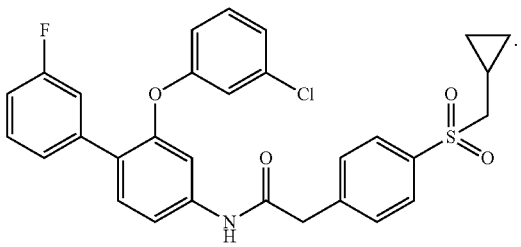

MS(ES⁺) m/z 550.1 (M + H)⁺

5: N-[3-(3-chlorophenoxy)-4-(3,4-difluorophenyl)phenyl]-2-(4-cyclopropylmethanesulfonylphenyl)acetamide

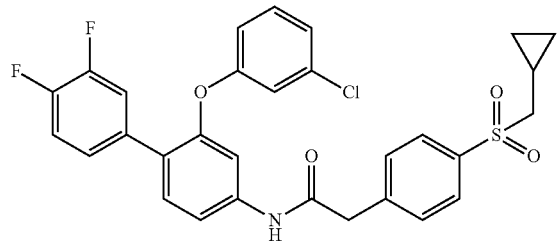

MS(ES⁺) m/z 568.1 (M + H)⁺

6: N-[3-(3-cyanophenoxy)-4-(3,4-difluorophenyl)phenyl]-2-(4-cyclopropylmethanesulfonylphenyl)acetamide

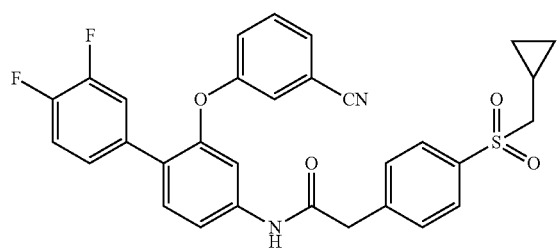

MS(ES⁺) m/z 559.2 (M + H)⁺

7: 2-(4-cyclopropylmethanesulfonylphenyl)-N-[3-(3-methoxyphenoxy)-4-(5-methyl-1H-pyrazol-1-yl)phenyl]acetamide

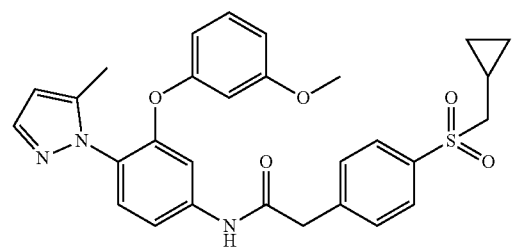

MS(ES⁺) m/z 532.2 (M + H)⁺

8: N-[3-(3-chlorophenoxy)-4-(3,5-difluorophenyl)phenyl]-2-(4-cyclopropylmethanesulfonylphenyl)acetamide

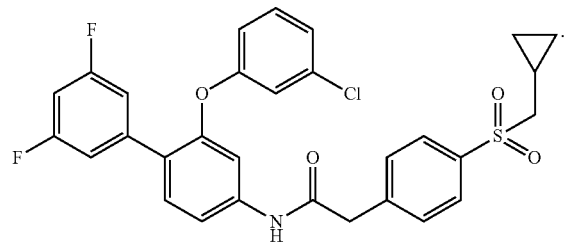

MS(ES⁺) m/z 567.1 (M + H)⁺

9: N-[4-(4-cyanophenyl)-3-(3-fluorophenoxy)phenyl]-2-(4-cyclopropylmethanesulfonylphenyl)acetamide

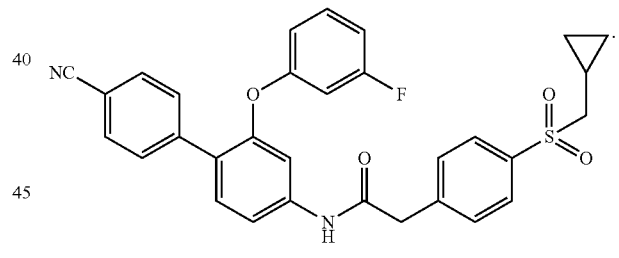

MS(ES⁺) m/z 541.2 (M + H)⁺

10: N-[3-(3-chlorophenoxy)-4-(3-cyanophenyl)phenyl]-2-(4-cyclopropylmethanesulfonylphenyl)acetamide

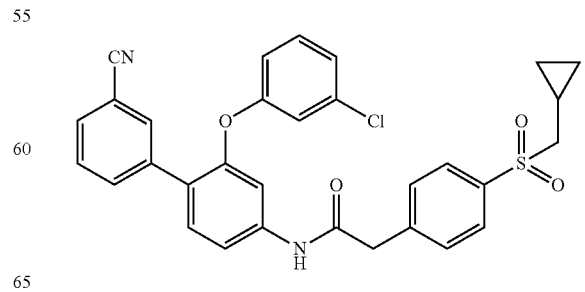

MS(ES⁺) m/z 557.1 (M + H)⁺

11: 2-(4-cyclopropylmethanesulfonylphenyl)-N-[4-(3-fluorophenyl)-3-[3-(trifluoromethyl)phenoxy]phenyl]acetamide

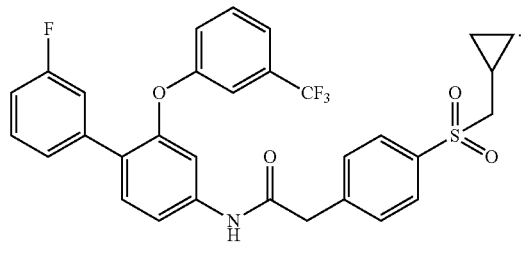

MS(ES⁺) m/z 584.2 (M + H)⁺

12: 2-(4-cyclopropylmethanesulfonylphenyl)-N-[3-(3-fluorophenoxy)-4-(4-fluorophenyl)phenyl]acetamide

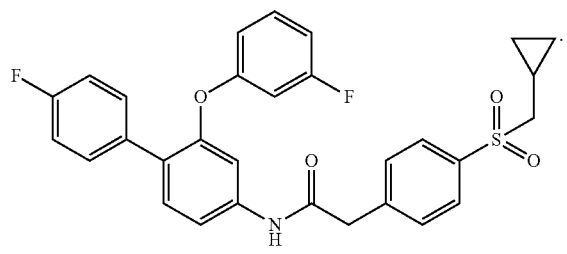

MS(ES⁺) m/z 534.2 (M + H)⁺

13: 2-(4-cyclopropylmethanesulfonylphenyl)-N-[3-(3,5-difluorophenoxy)-4-(3-fluorophenyl)phenyl]acetamide

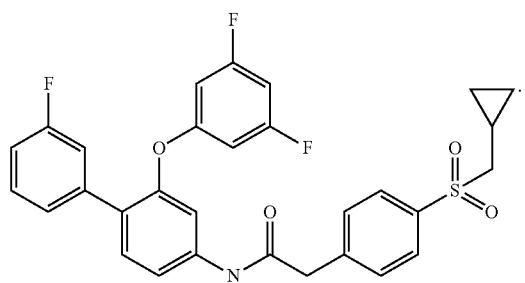

MS(ES⁺) m/z 552.2 (M + H)⁺

14: 2-[4-(cyclopropylsulfamoyl)phenyl]-N-[3-(3-methoxyphenoxy)-4-(4-methyl-1H-imidazol-1-yl)phenyl]acetamide

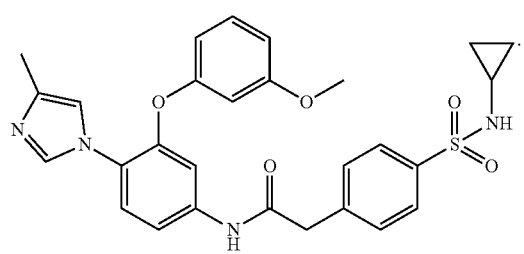

MS(ES⁺) m/z 533.2 (M + H)⁺

15: 2-[4-(cyclopropylsulfamoyl)phenyl]-N-[3-(3-methoxyphenoxy)-4-(5-methyl-1H-pyrazol-1-yl)phenyl]acetamide

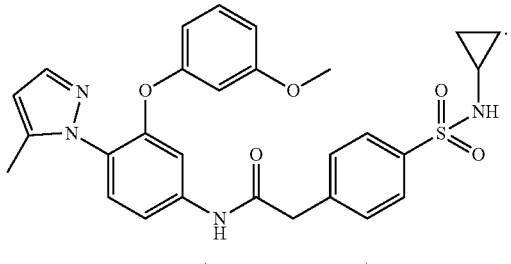

MS(ES⁺) m/z 533.2 (M + H)⁺

16: 2-[4-(cyclopropylsulfamoyl)phenyl]-N-[4-(3-fluorophenyl)-3-(3-methoxyphenoxy)phenyl]acetamide

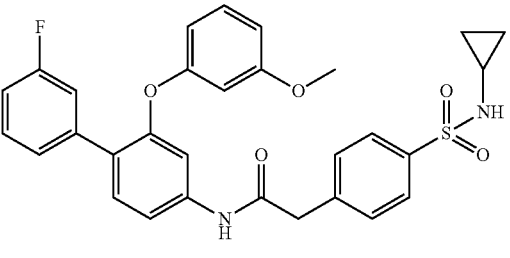

MS(ES⁺) m/z 547.2 (M + H)⁺

17: N-[3-(3-chlorophenoxy)-4-(3-fluorophenyl)phenyl]-2-[4-(cyclopropylsulfamoyl)phenyl]acetamide

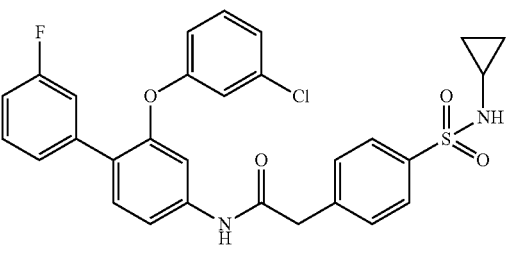

MS(ES⁺) m/z 551.2 (M + H)⁺

18: N-[3-(3-chlorophenoxy)-4-(3,4-difluorophenyl)phenyl]-2-[4-(cyclopropylsulfamoyl)phenyl]acetamide

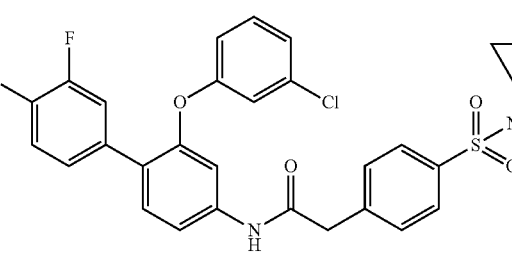

MS(ES⁺) m/z 569.2 (M + H)⁺

19: 2-[4-(cyclopropylsulfamoyl)phenyl]-N-[4-(3-fluorophenyl)-3-[3-(trifluoromethyl)phenoxy]phenyl]acetamide

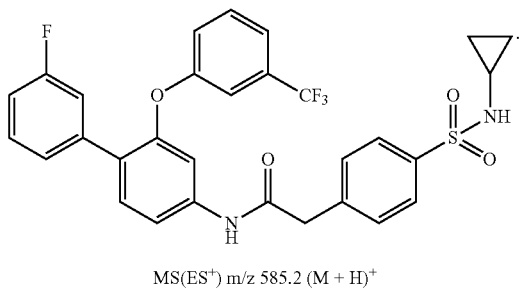 [SMILES: O=C(Cc1ccc(S(=O)(=O)NC2CC2)cc1)Nc1ccc(-c2cccc(F)c2)c(Oc2cccc(C(F)(F)F)c2)c1]

MS(ES+) m/z 585.2 (M + H)+

20: 2-(4-cyclopropylmethanesulfonylphenyl)-N-(5-phenoxy-4-phenyl-1,3-thiazol-2-yl)acetamide

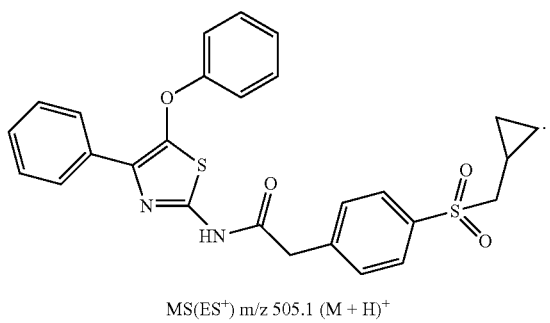 [SMILES: O=C(Cc1ccc(S(=O)(=O)CC2CC2)cc1)Nc1nc(-c2ccccc2)c(Oc2ccccc2)s1]

MS(ES+) m/z 505.1 (M + H)+

21: 2-(4-cyclopropylmethanesulfonylphenyl)-N-[4-phenyl-5-(pyridin-3-yloxy)-1,3-thiazol-2-yl]acetamide

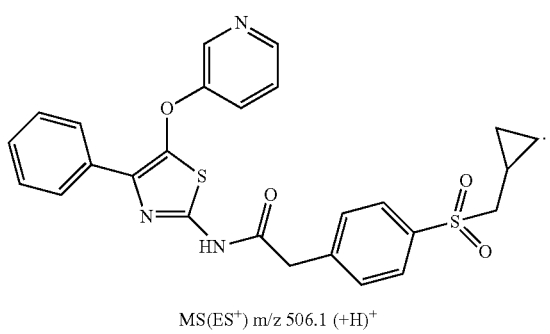 [SMILES: O=C(Cc1ccc(S(=O)(=O)CC2CC2)cc1)Nc1nc(-c2ccccc2)c(Oc2cccnc2)s1]

MS(ES+) m/z 506.1 (+H)+

22: N-(5-benzoyl-4-phenyl-1,3-thiazol-2-yl)-2-(4-cyclopropylmethanesulfonylphenyl)acetamide

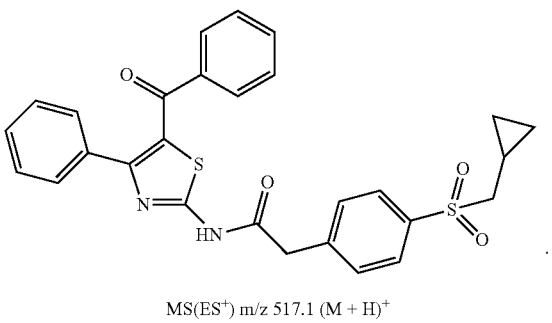 [SMILES: O=C(Cc1ccc(S(=O)(=O)CC2CC2)cc1)Nc1nc(-c2ccccc2)c(C(=O)c2ccccc2)s1]

MS(ES+) m/z 517.1 (M + H)+

23: N-[5-(4-chlorobenzoyl)-4-(3-chlorophenyl)-1,3-thiazol-2-yl]-2-(4-cyclopropylmethanesulfonylphenyl)acetamide

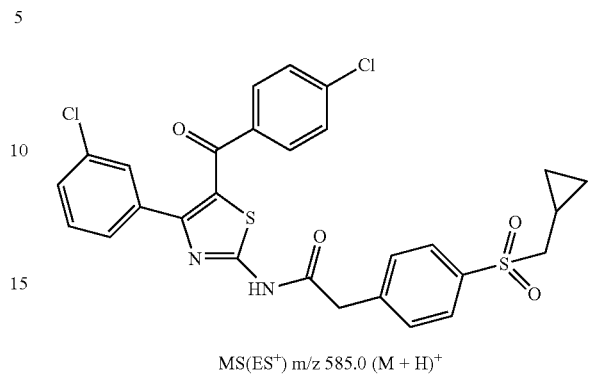

MS(ES+) m/z 585.0 (M + H)+

24: 2-(4-cyclopropylmethanesulfonylphenyl)-N-(4-phenylthiophen-2-yl)acetamide

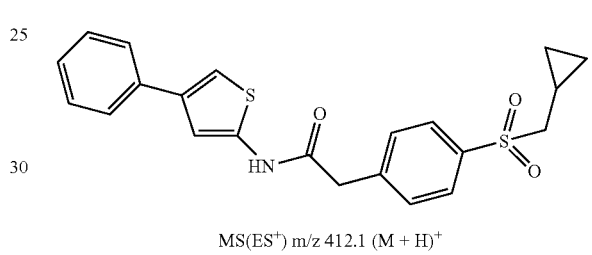

MS(ES+) m/z 412.1 (M + H)+

25: 2-(4-cyclopropylmethanesulfonylphenyl)-N-[4-(pyridin-3-yl)thiophen-2-yl]acetamide

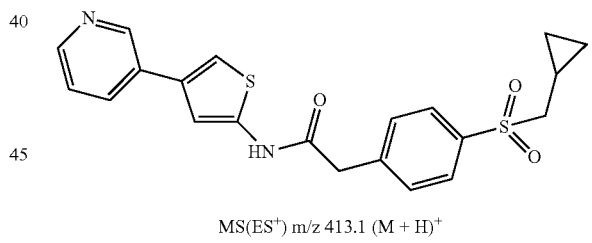

MS(ES+) m/z 413.1 (M + H)+

26: N-(5-benzoyl-4-phenyl-1,3-thiazol-2-yl)-2-[4-(cyclopropylsulfamoyl)phenyl]acetamide

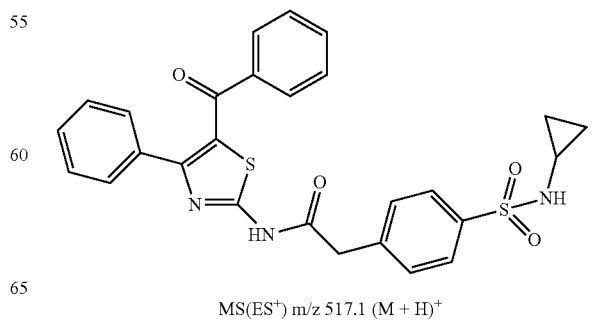

MS(ES+) m/z 517.1 (M + H)+

27: N-(5-benzoyl-4-phenylthiophen-2-yl)-2-(4-cyclopropylmethanesulfonylphenyl)acetamide

MS(ES+) m/z 516.1 (M + H)+

28: N-{3-chloro-4-[2-(trifluoromethoxy)phenyl]phenyl}-2-(4-cyclopropylmethanesulfonylphenyl)acetamide

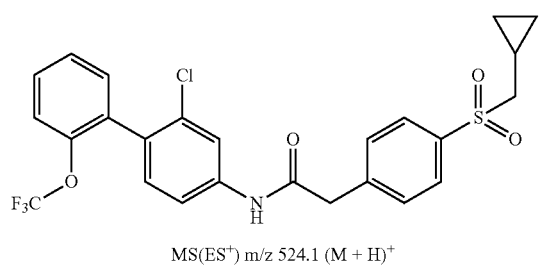

MS(ES+) m/z 524.1 (M + H)+

29: 2-(4-cyclopropylmethanesulfonylphenyl)-N-{3-methyl-4-[2-(trifluoromethoxy)phenyl]phenyl}acetamide

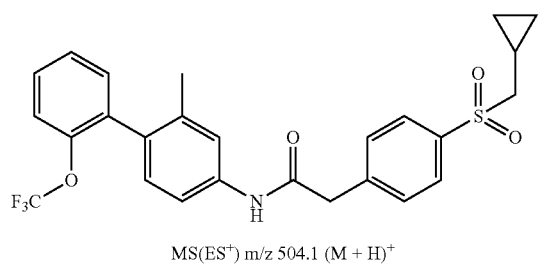

MS(ES+) m/z 504.1 (M + H)+

30: 2-(4-cyclopropylmethanesulfonylphenyl)-N-{3,5-dichloro-4-[2-(trifluoromethoxy)phenyl]phenyl}acetamide

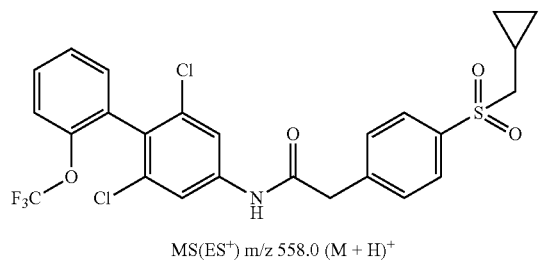

MS(ES+) m/z 558.0 (M + H)+

31: 2-(4-cyclopropylmethanesulfonylphenyl)-N-{4-methyl-5-[2-(trifluoromethoxy)phenyl]pyridin-2-yl}acetamide

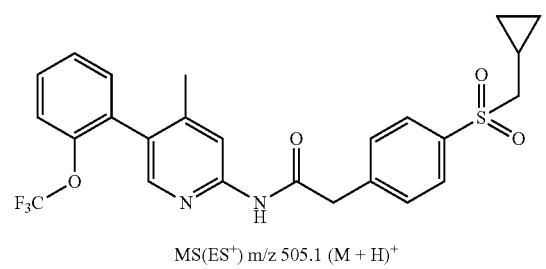

MS(ES+) m/z 505.1 (M + H)+

32: 2-(4-cyclopropylmethanesulfonylphenyl)-N-{6-methyl-5-[2-(trifluoromethoxy)phenyl]pyridin-2-yl}acetamide

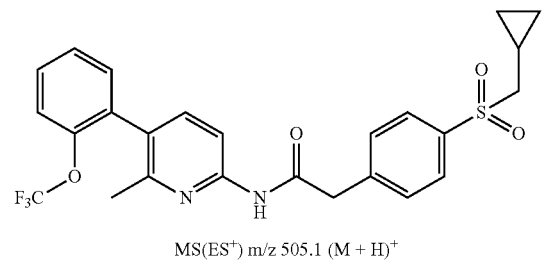

MS(ES+) m/z 505.1 (M + H)+

33: N-{3-chloro-4-[2-(trifluoromethoxy)phenyl]phenyl}-2-[4-(cyclopropylsulfamoyl)phenyl]acetamide

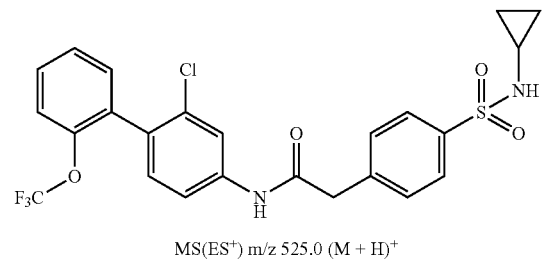

MS(ES+) m/z 525.0 (M + H)+

34: 2-[4-(cyclopropylsulfamoyl)phenyl]-N-{6-methyl-5-[2-(trifluoromethoxy)phenyl]pyridin-2-yl}acetamide

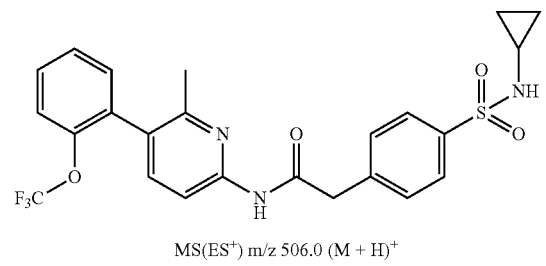

MS(ES+) m/z 506.0 (M + H)+

35: 2-[4-(cyclopropylsulfamoyl)phenyl]-N-{4-methyl-5-[2-(trifluoromethoxy)phenyl]pyridin-2-yl}acetamide

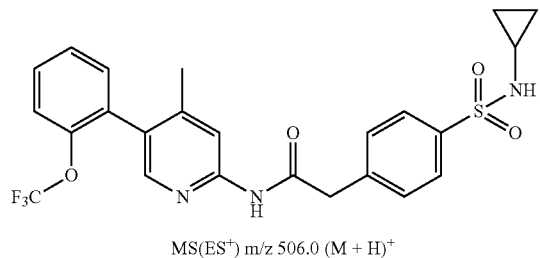

MS(ES+) m/z 506.0 (M + H)+

36: 2-[4-(cyclopropylsulfamoyl)phenyl]-N-{3-methyl-4-[2-(trifluoromethoxy)phenyl]phenyl}acetamide

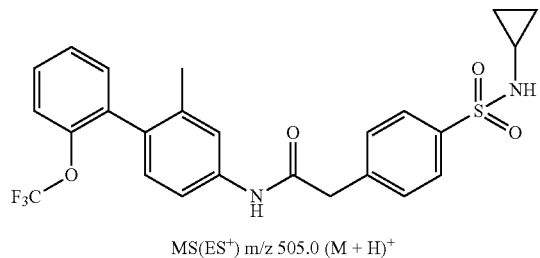

MS(ES+) m/z 505.0 (M + H)+

37: 2-(4-cyclopropylmethanesulfonylphenyl)-N-{4,6-dimethyl-5-[2-(trifluoromethoxy)phenyl]pyridin-2-yl}acetamide

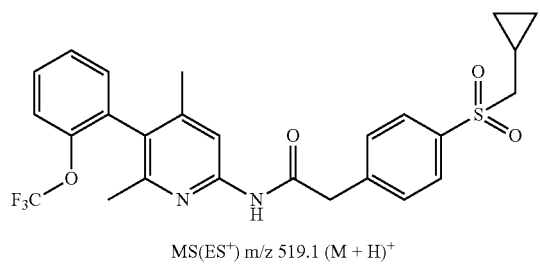

MS(ES+) m/z 519.1 (M + H)+

38: 2-(4-cyclopropylmethanesulfonylphenyl)-N-[4-(4-methyl-1H-imidazol-1-yl)phenyl]acetamide

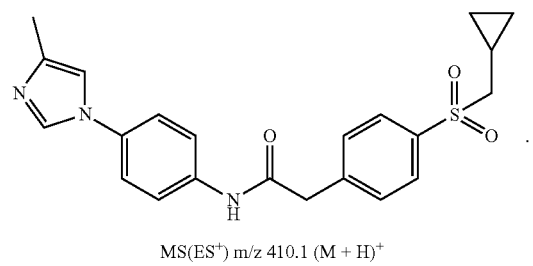 [SMILES: Cc1cn(-c2ccc(NC(=O)Cc3ccc(S(=O)(=O)CC4CC4)cc3)cc2)cn1]

MS(ES+) m/z 410.1 (M + H)+

39: 2-(4-cyclopropylmethanesulfonylphenyl)-N-[4-(5-methyl-1H-imidazol-1-yl)phenyl]acetamide

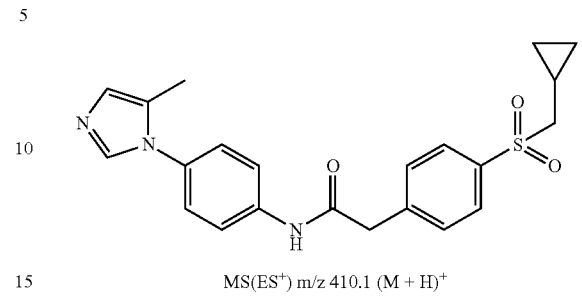

MS(ES+) m/z 410.1 (M + H)+

40: 2-(4-cyclopropylmethanesulfonylphenyl)-N-[4-(3-methyl-1H-pyrazol-1-yl)phenyl]acetamide

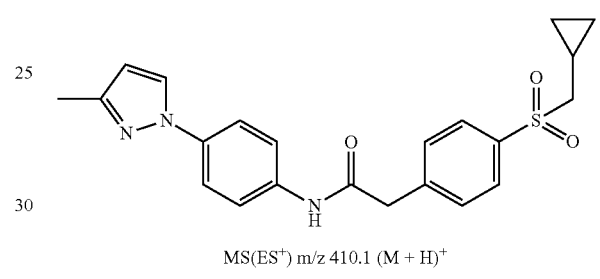

MS(ES+) m/z 410.1 (M + H)+

41: 2-(4-cyclopropylmethanesulfonylphenyl)-N-[4-(5-methyl-1H-pyrazol-1-yl)phenyl]acetamide

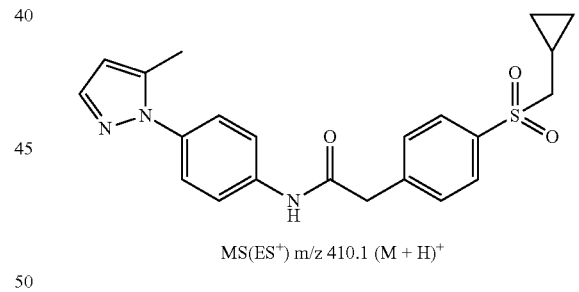

MS(ES+) m/z 410.1 (M + H)+

42: 2-(4-cyclopropylmethanesulfonylphenyl)-N-[4-(4-methyl-1H-pyrazol-1-yl)phenyl]acetamide

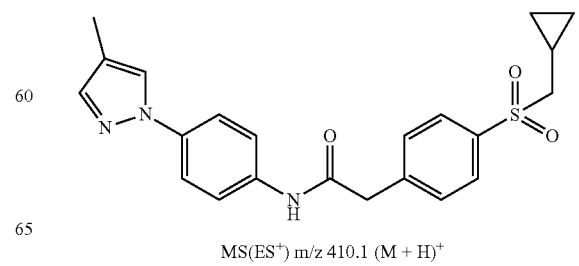

MS(ES+) m/z 410.1 (M + H)+

43: 2-(4-cyclopropylmethanesulfonylphenyl)-N-[4-(1,3-oxazol-5-yl)phenyl]acetamide

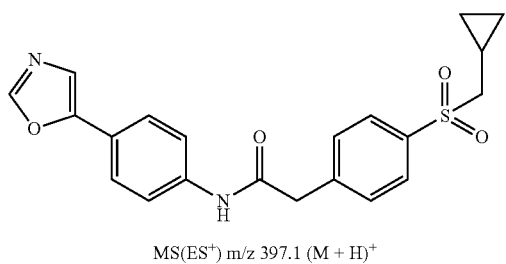

MS(ES⁺) m/z 397.1 (M + H)⁺

44: 2-(4-cyclopropylmethanesulfonylphenyl)-N-[4-(1H-pyrazol-1-yl)phenyl]acetamide

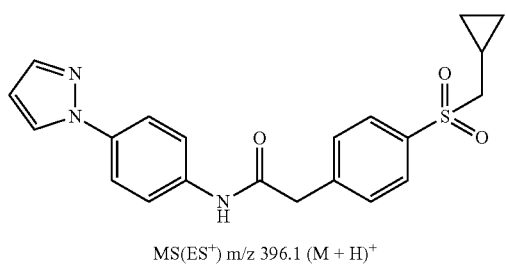

MS(ES⁺) m/z 396.1 (M + H)⁺

45: 2-(4-cyclopropylmethanesulfonylphenyl)-N-[4-(1H-imidazol-1-yl)phenyl]acetamide

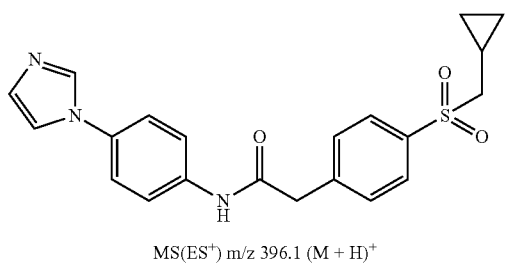

MS(ES⁺) m/z 396.1 (M + H)⁺

46: 2-(4-cyclopropylmethanesulfonylphenyl)-N-[4-(1H-1,2,4-triazol-1-yl)phenyl]acetamide

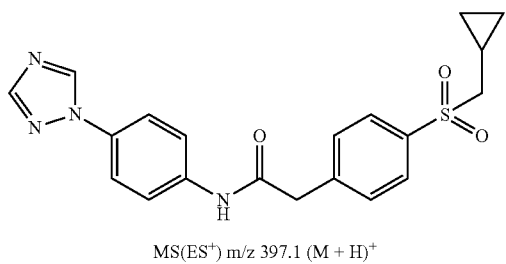

MS(ES⁺) m/z 397.1 (M + H)⁺

47: 2-(4-cyclopropylmethanesulfonylphenyl)-N-[4-(1,2,4-oxadiazol-3-yl)phenyl]acetamide

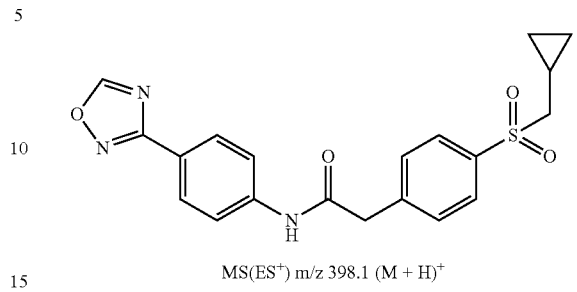

MS(ES⁺) m/z 398.1 (M + H)⁺

Example 48

RORγ GAL4 Reporter Gene Assay

Example inhibitors 1-47 were tested for their ability to inhibit RORγ activity in a RORγ GAL4 reporter gene assay. The assay procedure and results are described below.

RORγ GAL4 Reporter Gene Assay Description

A GAL4 one-hybrid reporter system employing luciferase readout was established to determine inhibition of RORγ in 293FT cells. The RORγ ligand-binding domain (LBD) was fused to the yeast GAL4 DNA binding domain (DBD) and placed under the control of the human cytomegalovirus (CMV) immediate early promoter, using expression vector pFN26A (Promega) and standard recombinant DNA cloning methods. To serve as a control in the assay, a similar vector was generated in which the GAL4-DBD was fused to Herpes simplex virus protein 16 (VP16), a constitutive transcriptional activator.

To monitor the inhibitory effect of compounds on RORγ, a transcriptional reporter construct was used. The pGL4.35 vector (Promega) contains nine copies of the GAL4 Upstream Activator Sequence (UAS). This sequence drives the transcription of the luciferase reporter gene luc2P in response to binding of a fusion protein containing the GAL4 DNA binding domain, as for example expressed by the GAL4-RORγ-LBD and GAL4-VP16 expression vectors described above. To allow a GAL4 fusion protein to drive the expression of the luciferase reporter, the pGL4.35 expression vector and the appropriate GAL4 fusion protein expression vector were bulk transfected in the 293FT cells using standard transfection techniques.

The day after transfection, cells were plated into 96 well plates, test compound was added and the plates were incubated overnight. Subsequently, the firefly luciferase activity was quantified using luciferase detection reagent and luminescence readout.

Detailed Assay Description

293FT cells (Invitrogen) were transfected with a GAL4 fusion protein expression vector (as described above) and the transcriptional reporter construct (pGL4.35, Promega). 60 µL of TransIT-293 transfection reagent (Mirus Bio) was added drop wise to 1500 µl Opti-MEM I Reduced Serum Medium (Invitrogen) and incubated at room temperature (RT) for 5 to 20 minutes. 1500 µL of this reagent mixture was added to 5 µg of GAL4 fusion protein expression vector and 5 µg of the transcriptional reporter construct, and incubated at RT for 20 minutes.

To harvest 293FT cells from a T75 flask, first the culture medium was taken off the cells. Subsequently, the cells were washed with Phosphate Buffered Saline (PBS) (Lonza), after which the PBS was removed. To dissociate the cells, 1 ml of TryPLE Express (Invitrogen) was added to the flask, followed by incubation at RT until the cells visually started to detach. Cells were collected in 5 mL of assay medium (DMEM culture medium (Lonza), 10% dialyzed FBS (Invitrogen) and Pen/Strep (Lonza)) to achieve a single cell suspension. $10 \times 10^6$ cells were spun down and re-suspended in 10 mL of assay medium. Subsequently, the cell suspension was added to the transfection mix tube, and then transferred as a whole to a T75 flask (Greiner), followed by overnight (16-24 hours) incubation at 37° C. and 5% $CO_2$.

For compound screening, the cells were harvested (as described above) and counted. $13 \times 10^6$ cells were spun down, the supernatant was aspirated and the cells were re-suspended in 17.3 mL of assay medium obtaining a cell suspension of $0.75 \times 10^6$ cells/mL. 80 μL of cell suspension (60,000 cells) was plated per well into a white, flat bottom, tissue culture treated, 96 well screening plates (Greiner).

Test compounds were diluted, starting from a 10 mM dimethylsulfoxide (DMSO) stock solution, to serial dilutions in DMSO at 500× the final test concentration. Subsequently, these solutions were diluted to 5× the final test concentration in two 10-fold-dilution steps in assay medium. The final DMSO concentration of the 5× test compound solution was 1%. 20 μL of the 5× test compound solution was added to each test well of the 96 well plate previously plated with 80 μl cell suspension, resulting in the final test concentration with 0.2% DMSO.

The plates were incubated overnight (16-24 hours) at 37° C. and 5% $CO_2$.

For the luciferase readout, the luciferase reagent (Britelite Plus, Perkin Elmer) was brought to RT. To each test well of the screening plates, 100 μL of 2.5-fold diluted Britelite Plus reagent was added, followed by incubation at RT for 10 minutes. The luciferase luminescence signal was measured using a Wallac Victor Microplate Reader (Perkin Elmer).

The half maximum inhibitory concentration ($IC_{50}$) values for the test compounds were calculated from the luciferase signal using GraphPad Prism software (GraphPad Software).

All exemplified compounds of Formula I (Examples 1-47) were found to have mean $pIC_{50}$ values above 5.

Examples 1-14, 16-37, 40-44, and 46-47 were found to have mean pIC50 values above or equal to 6.

Examples 2-13, 22, 23, 26-34, 36, and 37 were found to have mean pIC50 values above or equal to 7.

The invention claimed is:

1. A compound according to Formula I

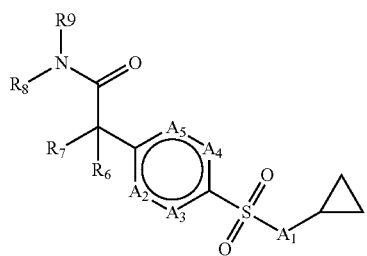

(Formula I)

or a pharmaceutically acceptable salt thereof wherein $A_1$ is $NR_1$ or $CR_1$, with $R_1$ being H or methyl, with methyl, if present, optionally being substituted with one or more F;

the cyclopropyl moiety can be optionally substituted with one or more methyl and one or more F;

$A_2, A_3, A_4$ and $A_5$ are independently N or $CR_2, CR_3, CR_4$ and $CR_5$, respectively, with the proviso that no more than two of the four positions A in $A_2, A_3, A_4$ and $A_5$ can be simultaneously N;

$R_2, R_3, R_4$, and $R_5$ are independently H, halogen, amino, C(1-3)alkoxy, (di)C(1-3)alkylamino or C(1-6)alkyl;

$R_6$ and $R_7$ are independently H, F, methyl, ethyl, hydroxyl or methoxy or $R_6$ and $R_7$ together is carbonyl, wherein methyl or ethyl groups, if present, may be optionally substituted with one or more F;

$R_8$ is H or C(1-6)alkyl;

R9 is selected from the group consisting of Formula II, III, IV and V

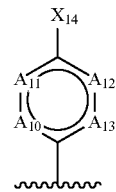

(Formula II)

wherein:

$A_{10}, A_{11}, A_{12}$, and $A_{13}$ are independently N or $CR_{10}, CR_{11}, CR_{12}$, and $CR_{13}$, respectively, with the proviso that no more than two of the four positions A in $A_{10}, A_{11}, A_{12}$, and $A_{13}$ can be simultaneously N;

$R_{10}, R_{11}, R_{12}$, and $R_{13}$ are independently H, halogen, amino, C(1-3)alkoxy, (di)C(1-3)alkylamino or C(1-6)alkyl;

$X_{14}$ is either C(6-10)aryl or C(1-9)heteroaryl, with all carbon atoms optionally substituted with halogen, amino, cyano, C(1-3)alkoxy, (di)C(1-3)alkylamino or C(1-3)alkyl;

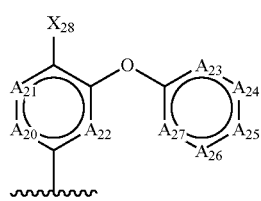

(Formula III)

wherein:

$A_{20}, A_{21}, A_{22}, A_{23}, A_{24}, A_{25}, A_{26}$ and $A_{27}$ are N or $CR_{20}, CR_{21}, CR_{22}, CR_{23}, CR_{24}, CR_{25}, CR_{26}$ and $CR_{27}$, respectively, with the proviso that no more than two of the three positions A in $A_{20}, A_{21}$ and $A_{22}$ can be simultaneously N and that no more than three of the five positions A in $A_{23}, A_{24}, A_{25}, A_{26}$ and $A_{27}$ can be simultaneously N;

$R_{20}, R_{21}$ and $R_{22}$ are independently H, halogen, amino, C(1-3)alkoxy, (di)C(1-3)alkylamino or C(1-6)alkyl;

$R_{23}, R_{24}, R_{25}, R_{26}$ and $R_{27}$ are independently H, halogen, amino, cyano, C(1-3)alkoxy, (di)C(1-3)alkylamino or C(1-3)alkyl;

$X_{28}$ is either C(6-10)aryl or C(1-9)heteroaryl, with all carbon atoms optionally substituted with halogen, amino, cyano, C(1-3)alkoxy, (di)C(1-3)alkylamino or C(1-3)alkyl;

(Formula IV)

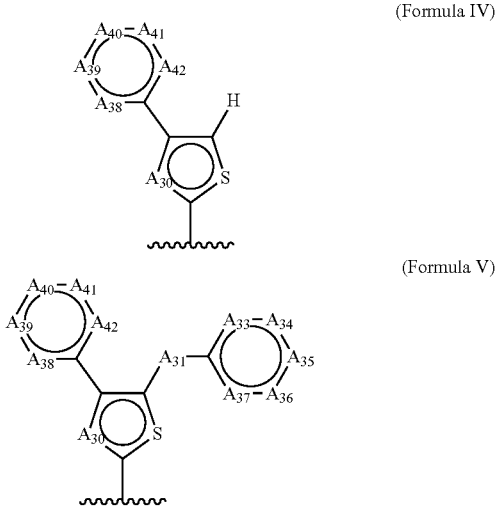

(Formula V)

wherein:
A$_{30}$ is N or C;
A$_{31}$ is O, carbonyl, NR$_{31}$ or CR$_{32}$;
R$_{31}$ is H or C(1-6)alkyl;
R$_{32}$ is H, OH, or C(1-3)alkyl, with all alkyl groups optionally substituted with one or more F or OH;
A$_{33}$, A$_{34}$, A$_{35}$, A$_{36}$, A$_{37}$, A$_{38}$, A$_{39}$, A$_{40}$, A$_{41}$ and A$_{42}$ are N or CR$_{33}$, CR$_{34}$, CR$_{35}$, CR$_{36}$, CR$_{37}$, CR$_{38}$, CR$_{39}$, CR$_{40}$, CR$_{41}$ and CR$_{42}$ respectively, with the proviso that no more than three of the five positions A in A$_{33}$, A$_{34}$, A$_{35}$, A$_{36}$ and A$_{37}$ can be simultaneously N and that no more than three of the five positions A in A$_{38}$, A$_{39}$, A$_{40}$, A$_{41}$ and A$_{42}$ can be simultaneously N;
R$_{33}$, R$_{34}$, R$_{35}$, R$_{36}$, R$_{37}$, R$_{38}$, R$_{39}$, R$_{40}$, R$_{41}$ and R$_{42}$ are independently H, halogen, amino, cyano, C(1-3) alkoxy, (di)C(1-3)alkylamino or C(1-3)alkyl.

2. The compound according to claim 1 where A$_1$ is CR$_1$.
3. The compound according to claim 1 where A$_1$ is NR$_1$.
4. The compound according to claim 1 where R$_1$ is hydrogen.
5. The compound according to claim 1 wherein R$_6$, and R$_7$ are both H.
6. The compound according to claim 1 where R$_8$ is H.
7. The compound according to claim 1 wherein all positions A in A$_2$, A$_3$, A$_4$ and A$_5$ are CR$_2$, CR$_3$, CR$_4$ and CR$_5$, and all positions R in R$_2$, R$_3$, R$_4$ and R$_5$ are H.
8. The compound according to claim 1 where R9 is according to Formula II wherein:
A$_{10}$, A$_{11}$, A$_{12}$ and A$_{13}$ are N or CR$_{10}$, CR$_{11}$, CR$_{12}$ and CR$_{13}$ respectively, with the proviso that no more than two of the four positions A in A$_{10}$, A$_{11}$, A$_{12}$ and A$_{13}$ can be simultaneously N;
R$_{10}$, R$_{11}$, R$_{12}$ and R$_{13}$ are independently H, amino, halogen, C(1-3)alkoxy, (di)C(1-3)alkylamino or C(1-6)alkyl;
X$_{14}$ is either C(6)aryl or C(1-5)heteroaryl, with all carbon atoms optionally substituted with halogen, cyano, C(1-3)alkoxy, (di)C(1-3)alkylamino or C(1-3)alkyl.
9. The compound according to claim 1 where R9 is according to Formula III wherein:
A$_{20}$, A$_{21}$, A$_{22}$, A$_{23}$, A$_{24}$, A$_{25}$, A$_{26}$ and A$_{27}$ are N or CR$_{20}$, CR$_{21}$, CR$_{22}$, CR$_{23}$, CR$_{24}$, CR$_{25}$, CR$_{26}$ and CR$_{27}$ respectively, with the proviso that no more than two of the three positions A in A$_{20}$, A$_{21}$ and A$_{22}$ can be simultaneously N and that no more than three of the five positions A in A$_{23}$, A$_{24}$, A$_{25}$, A$_{26}$ and A$_{27}$ can be simultaneously N;
R$_{20}$, R$_{21}$ and R$_{22}$ are independently H, halogen, amino, C(1-3)alkoxy, (di)C(1-3)alkylamino or C(1-6)alkyl;
R$_{23}$, R$_{24}$, R$_{25}$, R$_{26}$ and R$_{27}$ are independently H, halogen, cyano, amino, C(1-3)alkoxy, (di)C(1-3)alkylamino or C(1-3)alkyl;
X$_{28}$ is either C(6)aryl or C(1-5)heteroaryl, with all carbon atoms optionally substituted with halogen, cyano, C(1-3)alkoxy, (di)C(1-3)alkylamino or C(1-3)alkyl.
10. The compound according to claim 1 where R9 is according to Formula IV or V wherein:
A$_{30}$ is N or C;
A$_{31}$ is O, carbonyl, NR$_{31}$ or CR$_{32}$;
R$_{31}$ is H or C(1-6)alkyl;
R$_{32}$ is H, OH or C(1-6)alkyl, with all alkyl groups optionally substituted with one or more F or OH;
A$_{33}$, A$_{34}$, A$_{35}$, A$_{36}$, A$_{37}$, A$_{38}$, A$_{39}$, A$_{40}$, A$_{41}$ and A$_{42}$ are N or CR$_{33}$, CR$_{34}$, CR$_{35}$, CR$_{36}$, CR$_{37}$, CR$_{38}$, CR$_{39}$, CR$_{40}$, CR$_{41}$ and CR$_{42}$ respectively, with the proviso that no more than three of the five positions A$_{33}$, A$_{34}$, A$_{35}$, A$_{36}$ and A$_{37}$ can be simultaneously N and that no more than three of the five positions A$_{38}$, A$_{39}$, A$_{40}$, A$_{41}$ and A$_{42}$ can be simultaneously N;
R$_{33}$, R$_{34}$, R$_{35}$, R$_{36}$, R$_{37}$, R$_{38}$, R$_{39}$, R$_{40}$, R$_{41}$ and R$_{42}$ are independently H, halogen, cyano, C(1-3)alkoxy, (di)C(1-3)alkylamino or C(1-3)alkyl.
11. The compound as defined in claim 1 which is selected from the group of:
2-(4-cyclopropylmethanesulfonylphenyl)-N-(3-phenoxy-4-phenylphenyl)acetamide;
2-(4-cyclopropylmethanesulfonylphenyl)-N-[4-(3-fluorophenyl)-3-(3-methoxyphenoxy)phenyl]acetamide;
2-(4-cyclopropylmethanesulfonylphenyl)-N-[3-(3-methoxyphenoxy)-4-(4-methyl-1H-imidazol-1-yl)phenyl]acetamide;
N-[3-(3-chlorophenoxy)-4-(3-fluorophenyl)phenyl]-2-(4-cyclopropylmethanesulfonylphenyl)acetamide;
N-[3-(3-chlorophenoxy)-4-(3,4-difluorophenyl)phenyl]-2-(4-cyclopropylmethanesulfonylphenyl)acetamide;
N-[3-(3-cyanophenoxy)-4-(3,4-difluorophenyl)phenyl]-2-(4-cyclopropylmethanesulfonylphenyl)acetamide;
2-(4-cyclopropylmethanesulfonylphenyl)-N-[3-(3-methoxyphenoxy)-4-(5-methyl-1H-pyrazol-1-yl)phenyl]acetamide;
N-[3-(3-chlorophenoxy)-4-(3,5-difluorophenyl)phenyl]-2-(4-cyclopropylmethanesulfonylphenyl)acetamide;
N-[4-(4-cyanophenyl)-3-(3-fluorophenoxy)phenyl]-2-(4-cyclopropylmethanesulfonylphenyl)acetamide;
N-[3-(3-chlorophenoxy)-4-(3-cyanophenyl)phenyl]-2-(4-cyclopropylmethanesulfonylphenyl)acetamide;
2-(4-cyclopropylmethanesulfonylphenyl)-N-[4-(3-fluorophenyl)-3]3-(trifluoromethyl)phenoxy]phenyl]acetamide;
2-(4-cyclopropylmethanesulfonylphenyl)-N-[3-(3-fluorophenoxy)-4-(4-fluorophenyl)phenyl]acetamide;
2-(4-cyclopropylmethanesulfonylphenyl)-N-[3-(3,5-difluorophenoxy)-4-(3-fluorophenyl)phenyl]acetamide;
2-[4-(cyclopropylsulfamoyl)phenyl]-N-[3-(3-methoxyphenoxy)-4-(4-methyl-1H-imidazol-1-yl)phenyl]acetamide;
2-[4-(cyclopropylsulfamoyl)phenyl]-N-[3-(3-methoxyphenoxy)-4-(5-methyl-1H-pyrazol-1-yl)phenyl]acetamide;
2-[4-(cyclopropylsulfamoyl)phenyl]-N-[4-(3-fluorophenyl)-3-(3-methoxyphenoxy)phenyl]acetamide;

N-[3-(3-chlorophenoxy)-4-(3-fluorophenyl)phenyl]-2-[4-(cyclopropylsulfamoyl)phenyl]acetamide;
N-[3-(3-chlorophenoxy)-4-(3,4-difluorophenyl)phenyl]-2-[4-(cyclopropylsulfamoyl)phenyl]acetamide;
2-[4-(cyclopropylsulfamoyl)phenyl]-N-[4-(3-fluorophenyl)-3-[3-(trifluoromethyl)phenoxy]phenyl]acetamide;
2-(4-cyclopropylmethanesulfonylphenyl)-N-(5-phenoxy-4-phenyl-1,3-thiazol-2-yl)acetamide;
2-(4-cyclopropylmethanesulfonylphenyl)-N-[4-phenyl-5-(pyridin-3-yloxy)-1,3-thiazol-2-yl]acetamide;
N-(5-benzoyl-4-phenyl-1,3-thiazol-2-yl)-2-(4-cyclopropylmethanesulfonylphenyl)acetamide;
N-[5-(4-chlorobenzoyl)-4-(3-chlorophenyl)-1,3-thiazol-2-yl]-2-(4-cyclopropylmethanesulfonylphenyl)acetamide;
2-(4-cyclopropylmethanesulfonylphenyl)-N-(4-phenylthiophen-2-yl)acetamide;
2-(4-cyclopropylmethanesulfonylphenyl)-N-[4-(pyridin-3-yl)thiophen-2-yl]acetamide;
N-(5-benzoyl-4-phenyl-1,3-thiazol-2-yl)-2-[4-(cyclopropylsulfamoyl)phenyl]acetamide;
N-(5-benzoyl-4-phenylthiophen-2-yl)-2-(4-cyclopropylmethanesulfonylphenyl)acetamide;
N-{3-chloro-4-[2-(trifluoromethoxy)phenyl]phenyl}-2-(4-cyclopropylmethanesulfonylphenyl)acetamide;
2-(4-cyclopropylmethanesulfonylphenyl)-N-{3-methyl-4-[2-(trifluoromethoxy)phenyl]phenyl}acetamide;
2-(4-cyclopropylmethanesulfonylphenyl)-N-{3,5-dichloro-4-[2-(trifluoromethoxy)phenyl]phenyl}acetamide;
2-(4-cyclopropylmethanesulfonylphenyl)-N-{4-methyl-5-[2-(trifluoromethoxy)phenyl]pyridin-2-yl}acetamide;
2-(4-cyclopropylmethanesulfonylphenyl)-N-{6-methyl-5-[2-(trifluoromethoxy)phenyl]pyridin-2-yl}acetamide;
N-{3-chloro-4-[2-(trifluoromethoxy)phenyl]phenyl}-2-[4-(cyclopropylsulfamoyl)phenyl]acetamide;
2-[4-(cyclopropylsulfamoyl)phenyl]-N-{6-methyl-5-[2-(trifluoromethoxy)phenyl]pyridin-2-yl}acetamide;
2-[4-(cyclopropylsulfamoyl)phenyl]-N-{4-methyl-5-[2-(trifluoromethoxy)phenyl]pyridin-2-yl}acetamide;
2-[4-(cyclopropylsulfamoyl)phenyl]-N-{3-methyl-4-[2-(trifluoromethoxy)phenyl]phenyl}acetamide;
2-(4-cyclopropylmethanesulfonylphenyl)-N-{4,6-dimethyl-5-[2-(trifluoromethoxy)phenyl]pyridin-2-yl}acetamide;
2-(4-cyclopropylmethanesulfonylphenyl)-N-[4-(4-methyl-1H-imidazol-1-yl)phenyl]acetamide;
2-(4-cyclopropylmethanesulfonylphenyl)-N-[4-(5-methyl-1H-imidazol-1-yl)phenyl]acetamide;
2-(4-cyclopropylmethanesulfonylphenyl)-N-[4-(3-methyl-1H-pyrazol-1-yl)phenyl]acetamide;
2-(4-cyclopropylmethanesulfonylphenyl)-N-[4-(5-methyl-1H-pyrazol-1-yl)phenyl]acetamide;
2-(4-cyclopropylmethanesulfonylphenyl)-N-[4-(4-methyl-1H-pyrazol-1-yl)phenyl]acetamide;
2-(4-cyclopropylmethanesulfonylphenyl)-N-[4-(1,3-oxazol-5-yl)phenyl]acetamide;
2-(4-cyclopropylmethanesulfonylphenyl)-N-[4-(1H-pyrazol-1-yl)phenyl]acetamide;
2-(4-cyclopropylmethanesulfonylphenyl)-N-[4-(1H-imidazol-1-yl)phenyl]acetamide;
2-(4-cyclopropylmethanesulfonylphenyl)-N-[4-(1H-1,2,4-triazol-1-yl)phenyl]acetamide and
2-(4-cyclopropylmethanesulfonylphenyl)-N-[4-(1,2,4-oxadiazol-3-yl)phenyl]acetamide.

12. A pharmaceutical composition, which comprises a compound of Formula I according to claim 1 or a pharmaceutically acceptable salt thereof and one or more pharmaceutically acceptable excipients.

13. A method for the treatment of rheumatoid arthritis, psoriasis, inflammatory bowel disease, Crohn's disease or multiple sclerosis comprising administering to a patent in need thereof the compound according to claim 1 or a pharmaceutically acceptable salt thereof.

14. A method for the treatment of osteoarthritis or asthma comprising administering to a patent in need thereof the compound according to claim 1 or a pharmaceutically acceptable salt thereof.

15. A method for the treatment of mucosal leishmaniasis comprising administering to a patent in need thereof the compound according to claim 1 or a pharmaceutically acceptable salt thereof.

16. A method for the treatment of Kawaski disease or Hashimoto's thyroiditis comprising administering to a patent in need thereof the compound according to claim 1 or a pharmaceutically acceptable salt thereof.

* * * * *